United States Patent [19]

Klinkhammer

[11] Patent Number: 5,137,039

[45] Date of Patent: Aug. 11, 1992

[54] TOOTH CLEANING DEVICE

[75] Inventor: Ronald W. Klinkhammer, Seattle, Wash.

[73] Assignee: Focus Development Corporation, Inc., Seattle, Wash.

[21] Appl. No.: 664,487

[22] Filed: Mar. 4, 1991

[51] Int. Cl.$^5$ ............................................. A45D 44/18
[52] U.S. Cl. .................................. 132/308; 132/309; 15/167.1; 15/167.2
[58] Field of Search ............. 128/62 A, 66; 15/159 A, 15/167.2, 167.1, 22 R; 132/308, 309

[56] References Cited

U.S. PATENT DOCUMENTS

| | | | |
|---|---|---|---|
| 301,644 | 7/1884 | Thompson | 128/62 A |
| 715,263 | 12/1902 | Haussmann | 128/62 A |
| 864,054 | 8/1907 | Abrams | 15/167.2 |
| 1,389,624 | 9/1921 | Carroll | 15/167.2 |
| 1,599,339 | 9/1926 | Loyd | 15/167.2 |
| 1,668,385 | 5/1928 | Szekely et al. | 15/167.2 |
| 1,709,262 | 4/1929 | Henderhan | 15/167.2 |
| 2,139,245 | 12/1938 | Ogden | 128/62 A |
| 2,196,284 | 4/1940 | Ackerman | 128/62 A |
| 2,317,485 | 4/1943 | Rider | 15/167.1 |
| 2,625,697 | 1/1953 | Cyser | 15/22 |
| 2,660,745 | 12/1953 | Yusco | 15/22 |
| 2,766,750 | 10/1956 | Darcissac | 128/62 A |
| 2,807,820 | 10/1957 | Dinhofer | 15/167.1 |
| 3,103,027 | 9/1963 | Birch | 15/110 |
| 3,103,679 | 9/1963 | Clemens | 15/167.1 |
| 3,368,553 | 2/1968 | Kirby | 128/62 A |
| 3,398,421 | 8/1968 | Rashbaum | 15/167 |
| 3,509,874 | 5/1970 | Stillman | 128/66 |
| 3,631,869 | 1/1972 | Espinosa | 132/323 |
| 3,640,291 | 2/1972 | Mizuno | 132/84 |
| 3,732,589 | 5/1973 | Burki | 15/22 R |
| 3,879,139 | 4/1975 | Dahl et al. | 401/135 |
| 3,953,907 | 5/1976 | Froidevaux | 15/167 A |
| 4,263,691 | 4/1981 | Pakarnseree | 15/167.1 |
| 4,449,266 | 5/1984 | Northemann et al. | 15/167 A |
| 4,486,914 | 12/1984 | Planten et al. | 15/167 A |
| 4,488,328 | 12/1984 | Hyman | 15/167 R |
| 4,535,761 | 8/1985 | Rabinowitz | 128/62 A |
| 4,610,045 | 9/1986 | Rauch | 15/167 R |
| 4,625,357 | 12/1986 | De Martino | 15/167 A |
| 4,638,520 | 1/1987 | Eickmann | 15/22 R |
| 4,654,922 | 4/1987 | Chen | 15/172 |
| 4,691,405 | 9/1987 | Reed | 15/201 |

Primary Examiner—Gene Mancene
Assistant Examiner—Frank A. LaViola
Attorney, Agent, or Firm—Christopher Duffy

[57] ABSTRACT

The device and method employ a pair of spaced jaws which have a tooth cleaning implement connected therewith, in the gap therebetween. In use, the jaws are straddled about a row of teeth, transverse thereof, and translated along the row opposite the inside and outside faces of the teeth. Various features enable the user to locate and "steer" the device, even when the jaws and implement are out-of-sight to him. Other features enable the user to count on the device itself to provide the "dynamics" with which we commonly use a conventional "tooth brush" when we manipulate it in our mouths from a point thereoutside. Still others enable the user to program or predetermine the "grip" of the device, transverse of the row, and to do so, moreover, in the context of having an interchangeable or replaceable tooth cleaning implement thereon which is adjustable in "grip" each time a new implement is substituted for an old. Other features enable the user to clean both gums and teeth alike, as well as to dislodge debris from any pockets at the gum line, and to clean the interstices between pairs of teeth. Still others enable him to flush away debris which is generated by the device during the various tooth cleaning operations. The various features include, among others, a taco shell-like cartridge unit which is insertable in the gap between the jaws to serve as a tooth cleaning implement, and a module for forming such a cartridge. Initially, the module has a bat-like, spread wing configuration, but it is sufficiently flexible and/or pliable to be folded into the generally U-shaped configuration of a cartridge unit. The various features also include certain bristle which are used in certain tooth brushing heads of the device.

38 Claims, 8 Drawing Sheets

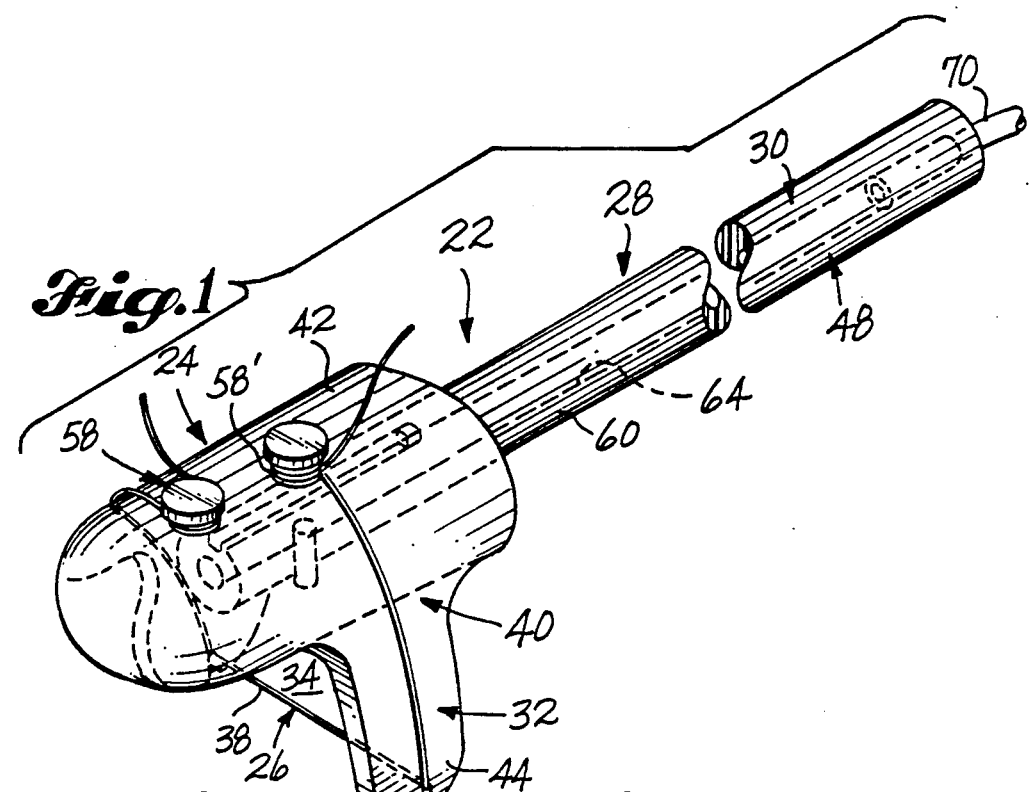
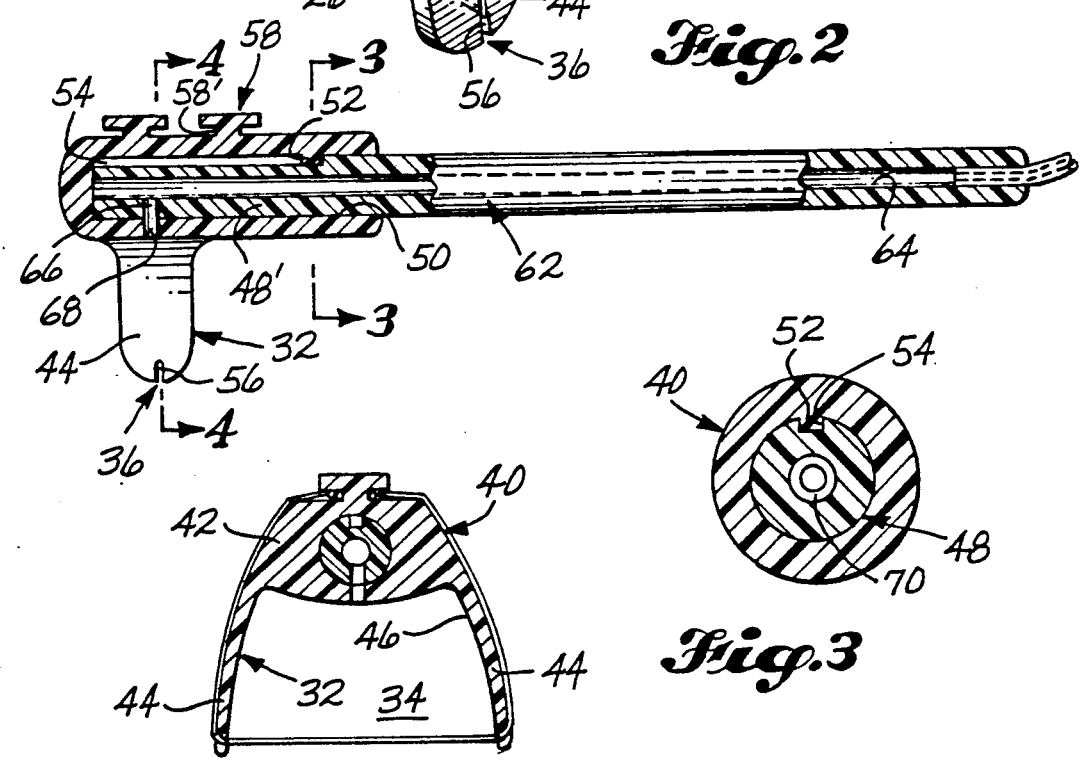

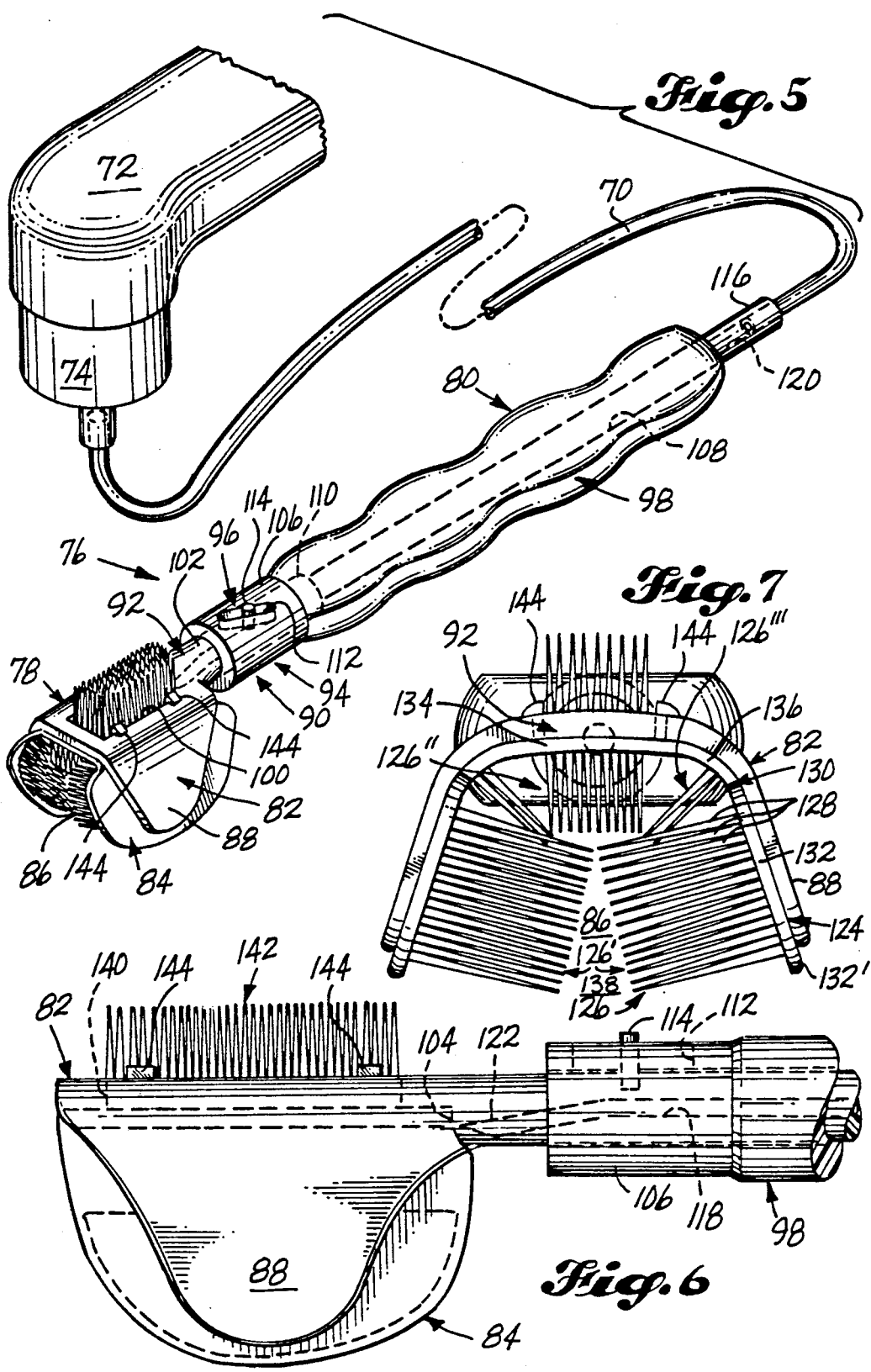

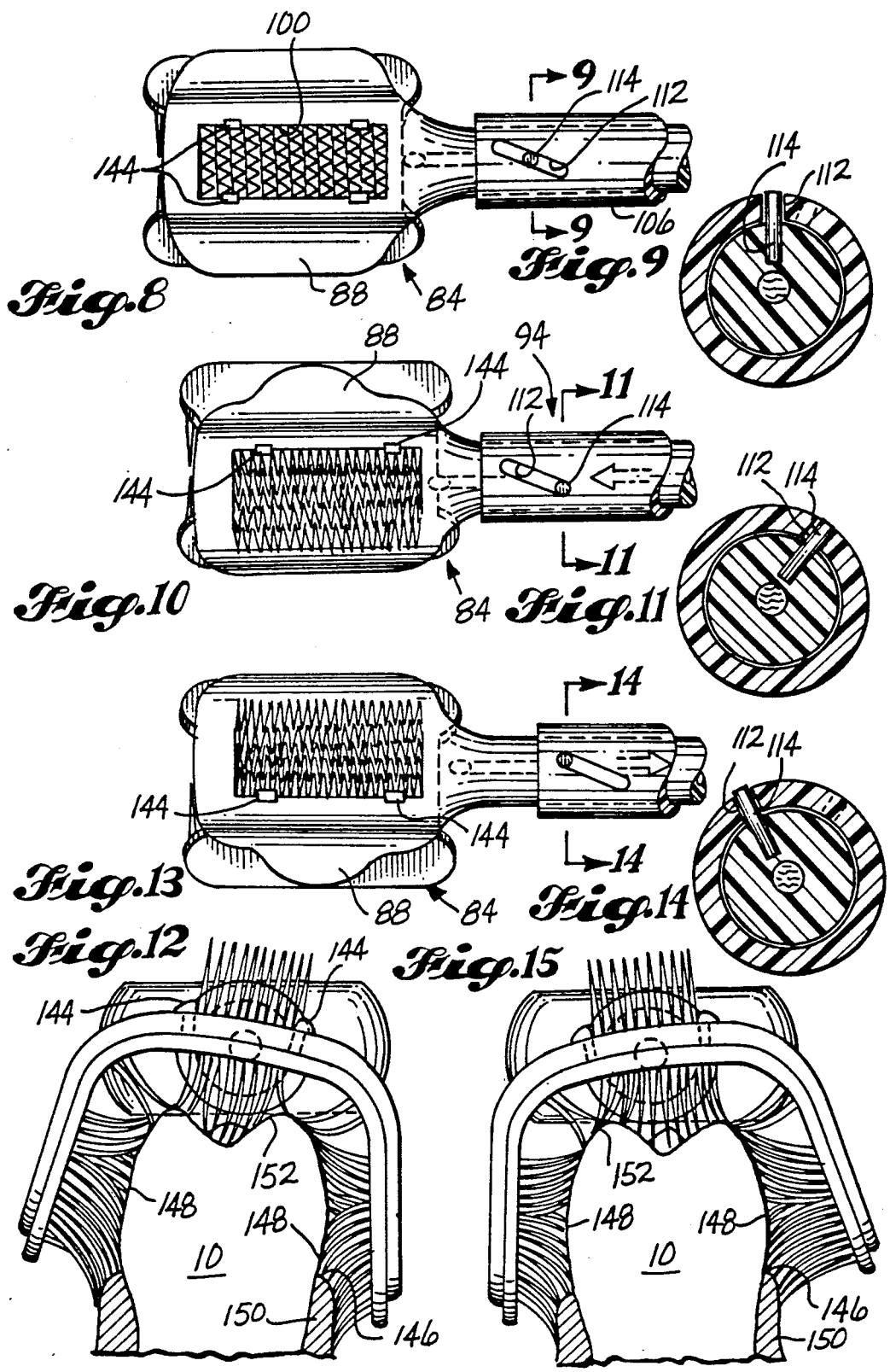

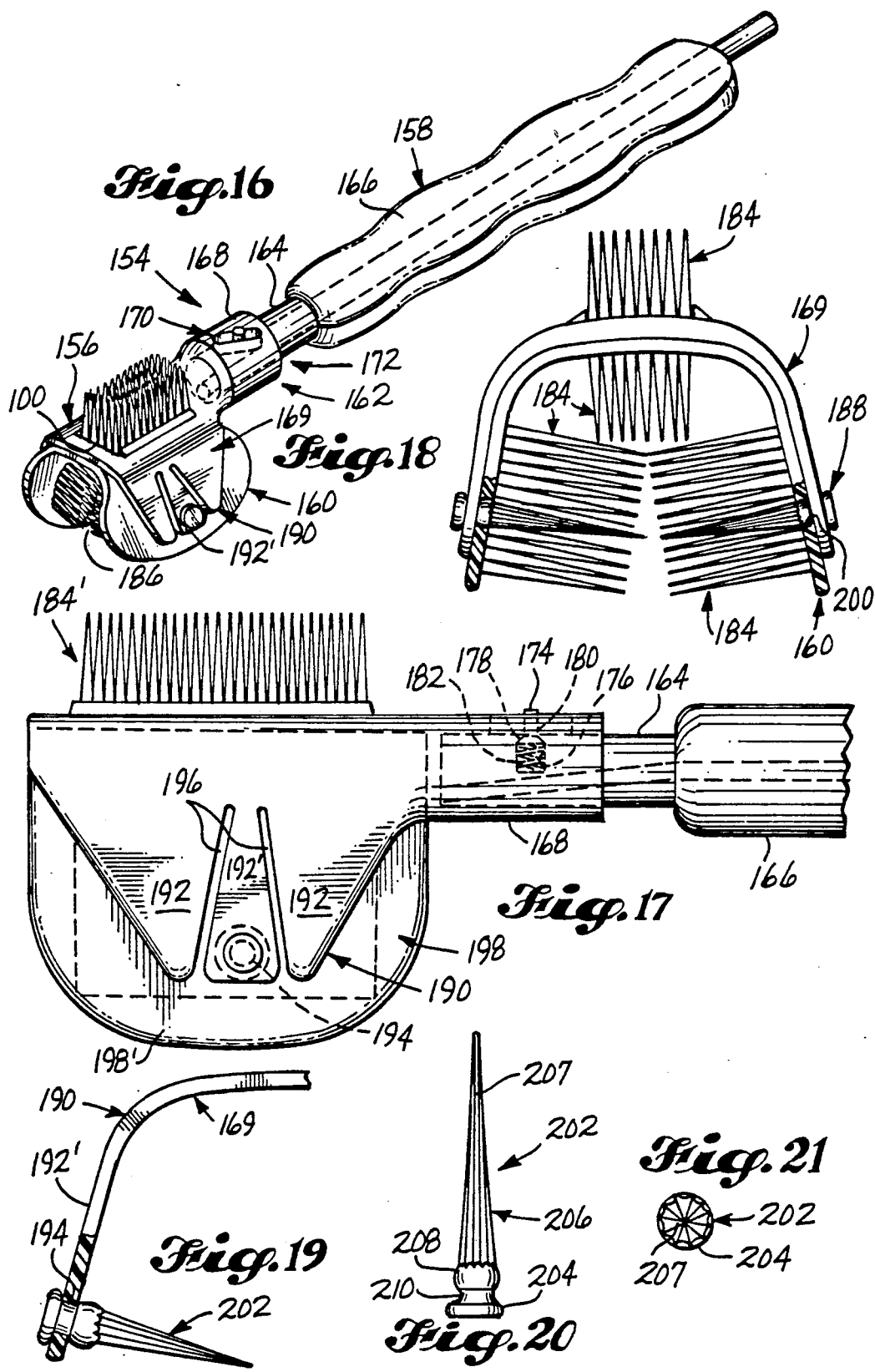

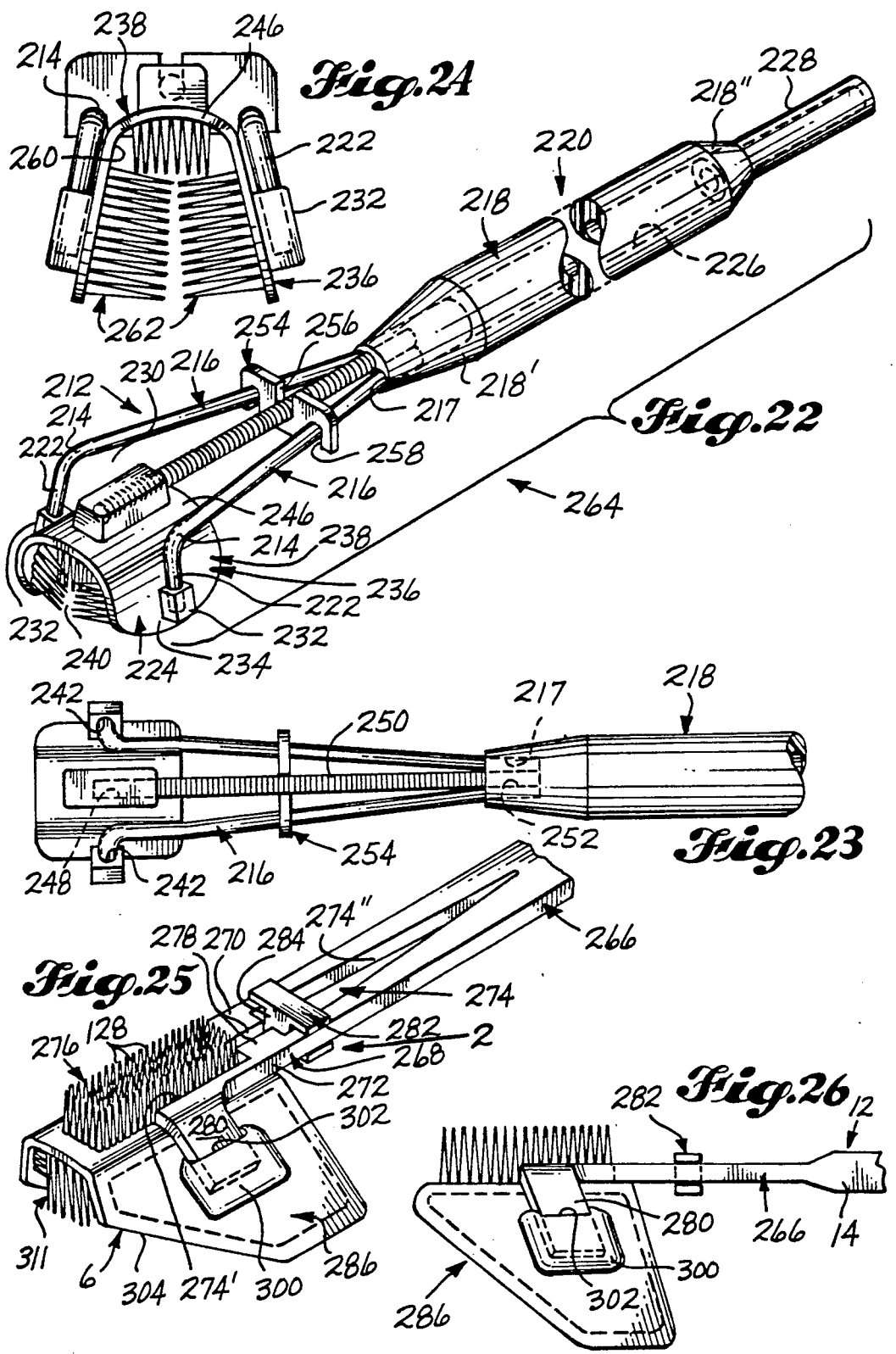

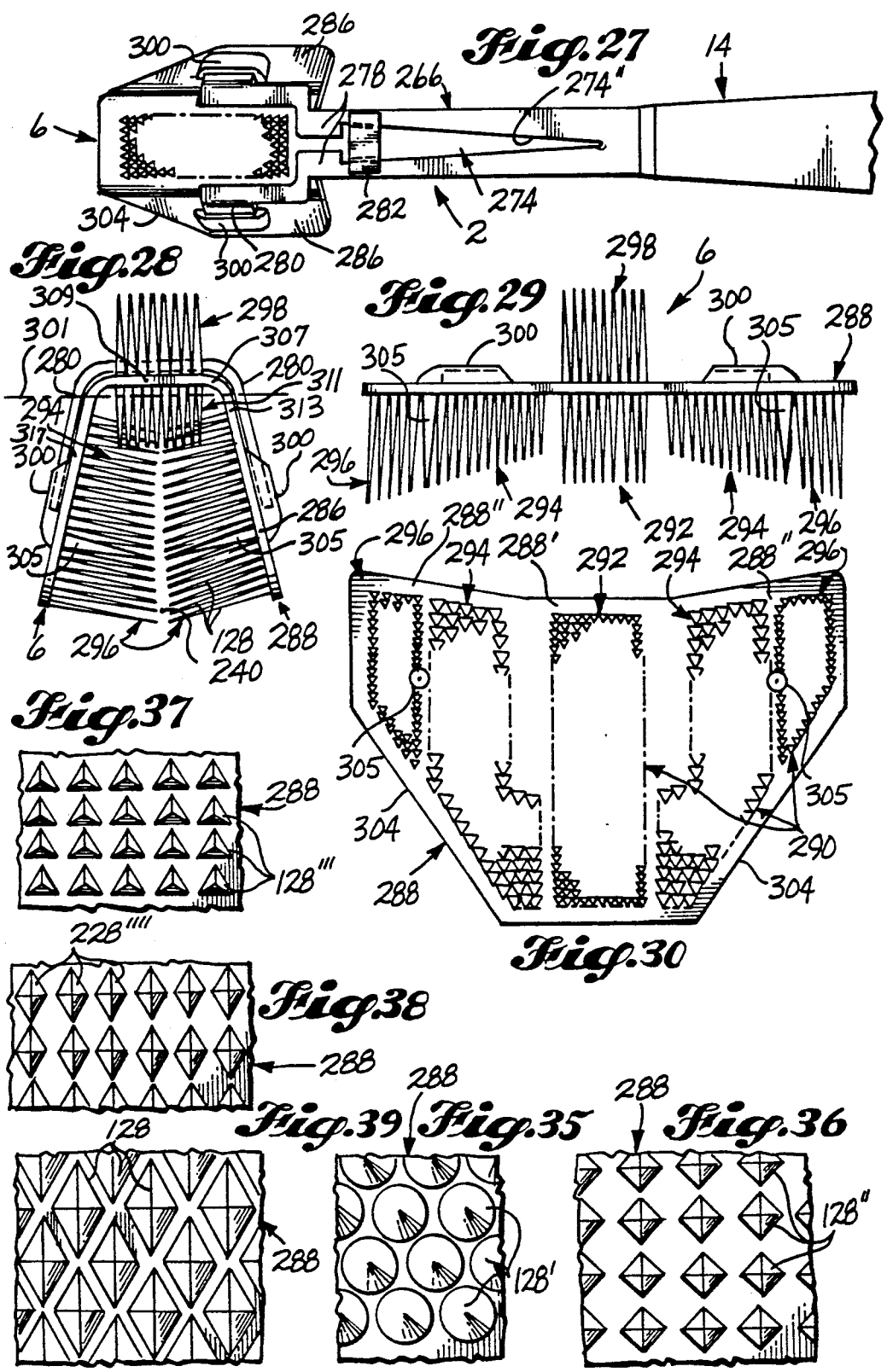

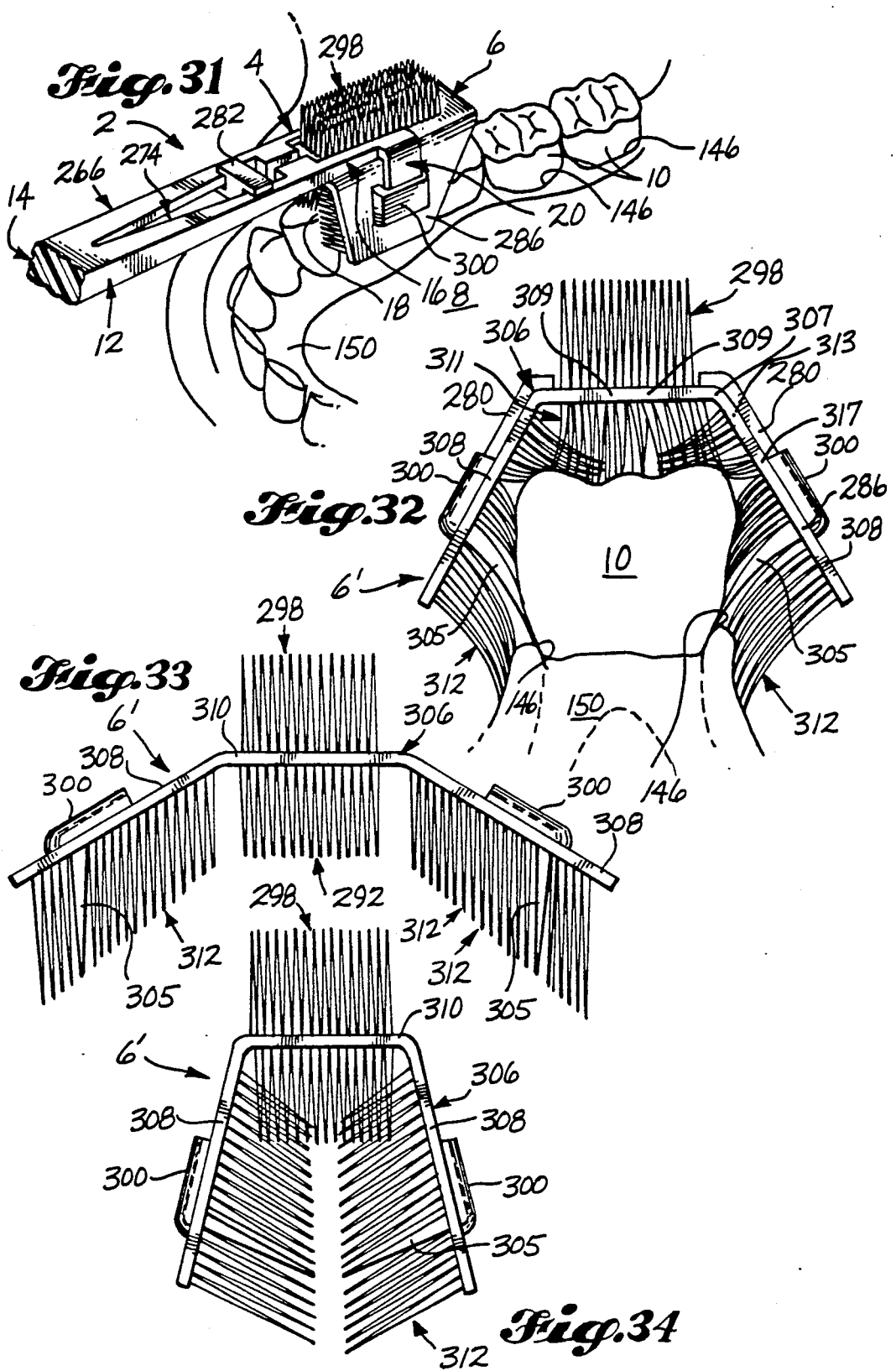

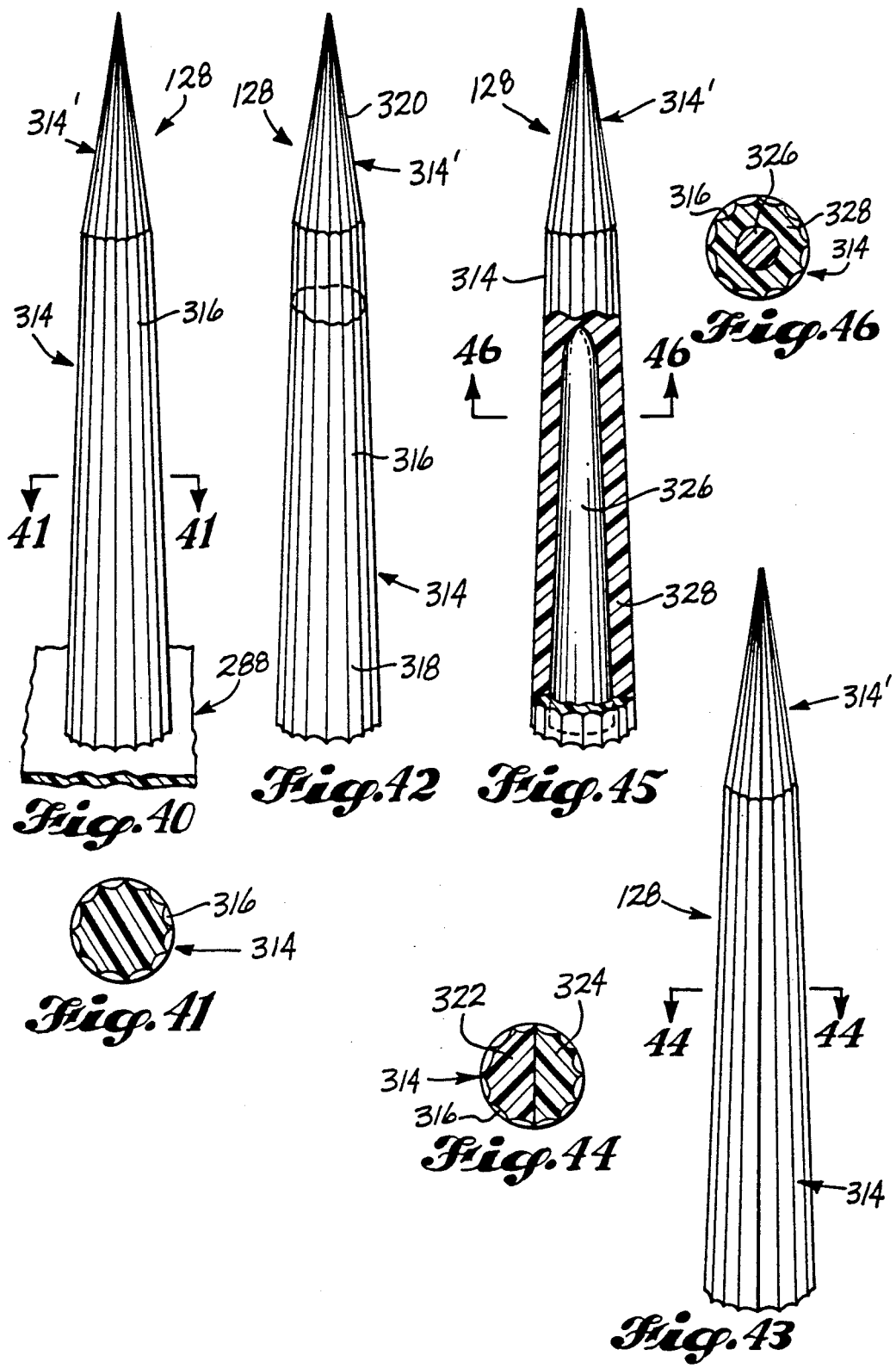

TOOTH CLEANING DEVICE

TECHNICAL FIELD

This invention relates to a tooth cleaning device and method, and in particular, to a hand-held device and method wherein a pair of spaced jaws which have a toothcleaning implement connected therewith, crosswise of the gap therebetween, are straddled about a row of teeth, transverse thereof, and translated along the row opposite the inside and outside faces of the teeth, to effect the cleaning operation.

BACKGROUND ART

Many such hand-held tooth brushing devices are known. For example, see U.S. Pat. No. 4,498,209, Australian Patent 449,836 and Belgium Patent 640,683. However, these prior devices do no more than enable a user to brush both faces of his teeth at one time, rather than doing them separately with a brush having a single set of bristle thereon. And in brushing the faces, he is largely limited to strokes lengthwise of a row. The devices themselves provide none of the additional "dynamics" or criss-cross action that we commonly put our brush through when brushing our teeth, and which we generate by raising and lowering the brush, by pressing harder or softer at times, and by swiveling the brush about our wrist, or about the palm of our hand with our fingers. All of this still must come from the user himself, and in the case of devices such as those shown in the Australian and Belgium patents, the user is largely prevented from generating these dynamics by the character of the device itself. In addition, in the case of a device such as that shown in U.S. Pat. No. 4,498,209, the user must adjust for himself, the light clamping action or "grip" with which the bristle are applied to the faces of the teeth; while in the case of devices such as those shown in the Australian and Belgium patents, he must be content with the predetermined grip provided by the device itself. Moreover, the user himself must locate and "steer" each device, and particularly the jaws and brushes or other implement on the same. He must, in effect, observe its path and guide the device by sight, to assure that it "tracks" along the faces, and equally importantly, the gums therebelow. There is no assurance that the device will sweep the gums unless he, himself, steers the device so that the bristle continue to bear against the gums throughout the operation. Any "moat-like" pockets between the teeth and gums, at the gum line, are left untouched, moreover, because the bristle do not have the firmness or rigidity of a "pick" to dislodge debris that may be collected on them. Also, neither device provides for cleaning the interstices between pairs of teeth, such as is commonly done with dental floss. And, in addition, neither provides for flushing away the debris which is generated during the various cleaning operations, whether from the faces of the teeth or from the interstices between pairs of teeth. Neither provides, too, for substituting a new tooth cleaning implement for an old one, when the life of the old one is spent; or for replacing an old implement with a new one, when the new one would be better suited to the task at hand; or as indicated, for adjusting the "grip" of each new implement when it is put to use on a device.

What is needed then, is a straddle-type tooth cleaning device which enables the user to program or predetermine the "grip" of the device, to locate and "steer" the device—even when the jaws and brushes or other implement are out of sight to him—and to count on the device itself to provide the "dynamics" with which we commonly use a conventional "tooth brush" when we manipulate it in our mouths from a point thereoutside. All of this is needed, moreover, in the context of one which has an interchangeable or replaceable tooth cleaning implement, and particularly one which is adjustable in "grip" each time a new implement is substituted. And furthermore, all of this is needed in the context of one which will clean both gums and teeth alike, as well as dislodge debris from any pockets at the gum line, and clean the interstices between pairs of teeth, as well as flush away the debris which is generated by the device during each of the various cleaning operations.

DISCLOSURE OF THE INVENTION

Such a device is provided by the present invention which meets all of the foregoing objectives, as well as others which will become apparent hereinafter. According to the invention, a tooth cleaning device is provided which comprises carrier means that have a tooth cleaning implement thereon and are adapted to be inserted with the implement in the mouth of the user, and positioned in his mouth adjacent a row of his teeth, for application of the implement thereto. The device also comprises elongated positioning means, including a handle, for supporting the carrier means adjacent the user's row of teeth. The carrier means are connected with the positioning means, adjacent the distal end thereof, and comprise a pair of jaws which are operatively spaced apart from one another, crosswise the longitudinal axis of the positioning means, to form a gap therebetween. The tooth cleaning implement is connected, in turn, with the carrier means, relatively crosswise of the gap between the jaws, and preferably there are connector means whereby the implement is detachably connected to the carrier means in this manner.

The device is embodied in many forms and these embodiments have many and varied ways of addressing the foregoing objectives. For example, to enable the user to generate the desired dynamics during the tooth cleaning operation, certain of the presently preferred embodiments of the device employ jaws which are responsive to being straddled about a row of teeth, transverse thereof, and translated along the row opposite the inside and outside faces of the teeth, to rotate in relation to the positioning means about the longitudinal axis thereof; and there are means in the device for converting the rotation of the jaws into oscillatory motion on the part of the implement, criss-cross of the teeth. Other embodiments employ jaws which are responsive to being straddled and translated along a row as indicated, to shift in relation to the positioning means along parallels to the longitudinal axis thereof; and there are means in the device for converting the axial shift of the jaws into oscillatory motion on the part of the implement, criss-cross of the teeth. Still further embodiments employ jaws which are both rotatable in relation to the positioning means about the longitudinal axis thereof and shiftable in relation to the positioning means along parallels to the longitudinal axis of the same when the jaws are straddled and translated along a row as indicated. In this instance, the device further comprises means for converting the relative rotation and axial shift of the jaws into oscillatory motion on the part of the implement, criss-cross of the teeth. To illustrate, in some of the latter embodiments, the carrier means are interconnected with the positioning means to undergo relative rotation and axial shift in relation to the same about and along the longitudinal axis thereof, but there are cam means in the connection between the carrier means and the positioning means which are operative to oscillate the carrier means crosswise the axis of the positioning means when the jaws are straddled about a row of teeth, transverse thereof, and translated along the row opposite the faces of the teeth as indicated. In many of this latter group of embodiments, for example, the carrier means and positioning means have a male/female connection therebetween, and there is a pin and slot connection interposed in the male/female connection to cause the carrier means to oscilate as indicated, when the jaws are straddled and translated along the row of teeth as indicated.

Certain additional embodiments of the device generate the desired dynamics by employing jaws which are reciprocable in relation to one another crosswise of the gap therebetween, and drive means which are reciprocable along parallels to the longitudinal axis of the positioning means to cause the jaws to reciprocate in relation to one another when the jaws are straddled about a row of teeth, transverse thereof, and translated along the row opposite the inside and outside faces of the teeth as indicated. In some of these embodiments, the jaws are formed on a pair of spaced arms which are reciprocable in relation to one another transverse the longitudinal axis of the positioning means, and there are cam means operatively interposed between the drive means and the arms to reciprocate the arms in relation to one another when the drive means are reciprocated along parallels to the longitudinal axis of the positioning means as indicated. In one group of embodiments, the arms are resiliently flexible and the cam means are responsive to reciprocation of the drive means to cause the arms to flex in relation to one another and thereby reciprocate the jaws in relation to one another. In some of the latter embodiments, the arms are cantilevered from the distal end of the positioning means, axially thereof, and the drive means include a manually driven member which is slidably engaged on the device to be reciprocated along the axis of the positioning means. In certain of these, the arms have cam surfaces on the relatively remote sides thereof which are disposed at an acute angle to one another, and the drive member takes the form of a drive element which is circumposed about the surfaces and slidably engaged with the same to flex the arms relatively toward one another when the element is reciprocated relatively away from the apex of the angle between the surfaces. In other embodiments, the arms have cam surfaces on the relatively adjacent sides thereof which are disposed at an acute angle to one another, and the drive member takes the form of a drive element which is interposed between the surfaces and slidably engaged with the same to flex the arms relatively away from one another when the element is reciprocated relatively toward the apex of the angle between the surfaces.

To enable the user to preset the grip of the device before it is put to use, many of the presently preferred embodiments of the device employ jaws which are shiftable in relation to one another transverse the longitudinal axis of the positioning means to adjust the width of the gap between the jaws; and there are retainer means in the device which are reciprocable along parallels to the longitudinal axis of the positioning means, to selected positions at which they are operable to fix the position of the jaws in relation to one another when the width of the gap has been adjusted. In some of these embodiments, the jaws are formed on a pair of spaced arms which are shiftable in relation to one another transverse the longitudinal axis of the positioning means, and there are cam means operatively interposed between the retainer means and the arms to fix the position of the arms in relation to one another when the retainer means have been reciprocated to a selected position corresponding to the adjusted width of the gap between the jaws. In one group of embodiments, the arms are resiliently flexible and the cam means are responsive to flexure of the arms to fix the position of the arms in relation to one another and thereby fix the position of the jaws in relation to one another when the width of the gap has been adjusted. In some of these latter embodiments, the arms are cantilevered from the distal end of the positioning means, axially thereof, and the retainer means include a manually driven member which is slidably engaged on the device to be reciprocated along the axis of the positioning means. In certain of these, the arms have cam surfaces on the relatively remote sides thereof which are disposed at an acute angle to one another, and the retainer member takes the form of a retainer element which is slidably circumposed about the surfaces and clampingly engaged with the same to fix the position of the arms in relation to one another when the arms have been flexed relatively toward one another to adjust the width of the gap between the jaws. In other embodiments, the arms have cam surfaces on the relatively adjacent sides thereof which are disposed at an acute angle to one another, and the retainer member takes the form of a retainer element which is slidably interposed between the surfaces and wedgingly engaged with the same to fix the position of the arms in relation to one another when the arms have been flexed relatively away from one another to adjust the width of the gap between the jaws.

In one special group of embodiments, the carrier means themselves are mounted on the positioning means to be moveable in relation thereto when the carrier means are straddled about a row of teeth, transverse thereof, and translated along the row so that the jaws thereof oppose the inside and outside faces of the teeth; and there are means in the device whereby the jaws are driven criss-cross the longitudinal axis of the positioning means in response to the movement of the carrier means, and drive means on the positioning means for oscillating the carrier means lengthwise the longitudinal axis thereof to produce movement in the carrier means. In this way, the device lends itself both to the required dynamics and/or to adjustment of its grip.

In many of this latter group, the various embodiments employ carrier means having a U-shaped body, the skirts of which form jaws having an open-ended slot therebetween. Assuming that the tooth cleaning operation is a brushing operation, this leaves the carrier means equipped to have a brush component on the inner periphery thereof, adjacent the bight of the same, as well as adjacent the jaws of the same. The carrier means may also have brush components in the corners of the same, and if desired, there may be a further brush component on the bight of the carrier means at the outer periphery thereof.

On the other hand, where the cleaning operation is a flossing operation, the carrier means need only have means thereon whereby an elongated string of dental floss can be detachably connected to the same in a taut condition crosswise the gap between the jaws. For example, the jaws may have notches therein for this purpose, whereby the string, as a closed loop or otherwise, can be releasably secured to the carrier means for the flossing operation.

To enable the user to flush away debris which is generated during the tooth cleaning operation, some presently preferred embodiments of the device further comprise fluid delivery means which are operable to discharge fluid into the gap between the jaws for this purpose. In many of these embodiments, the positioning means define a fluid flow passage which opens adjacent the gap between the jaws to discharge the fluid thereinto. In certain of them, the passage opens into the gap at a point on the connection between the carrier means and the positioning means. In other embodiments, the passage opens into the gap at a point on the carrier means.

To enable the tooth cleaning implement to be replaced or interchanged with another implement, certain embodiments of the device employ carrier means and positioning means which are detachably connected with one another. In many embodiments, the carrier means and positioning means have a pair of elements thereon which are cooperatively engaged with one another to form a male/female joint therebetween, and there are detent means in the joint which releasably secure the carrier and positioning means to one another. In some embodiments, for example, one element has mortise-like means thereon, and the other has tenon-like means thereon which are yieldably biased to engage in the mortise-like means.

Toward the same end, certain other embodiments of the device employ a tooth cleaning implement and carrier means which are detachably connected with one another. In many of these embodiments, the implement and carrier means have tenon and mortise-like means thereon which are cooperatively engaged with one another to form a male/female joint therebetween, and there are detainer means in the joint which releasably secure the implement and carrier means to one another. In certain of them, for example, the implement and carrier means have cooperatively engaged U-shaped bodies, and one body has mortise-like means on the bight thereof, and the other body has tenon-like means on the bight thereof which are engaged in the mortise-like means of the one body, transverse the longitudinal axis of the positioning means. In others, the implement and carrier means comprise pairs of oppositely disposed jaws. One pair of jaws has mortise-like means on the bodies thereof, and the other pair has tenon-like means on the bodies thereof which are engaged in the mortise-like means of the one pair of jaws, transverse the longitudinal axis of the positioning means. In still others, the implement and carrier means have pairs of oppositely disposed jaws on the bodies thereof. One pair of jaws has mortise-like means thereon, and the other pair of jaws are tenon-like in nature and engaged in the mortise-like means of the one pair of jaws, transverse the longitudinal axis of the positioning means.

The tenon and mortise-like means may be engaged in an interference fit which releasably secures the implement and carrier means to one another. Or, the mortise-like means may be open-ended and the tenon-like means may have resiliently laterally displaceable detent means on the forward end portion thereof which are engaged with the mortise-like means at the open end thereof. Or, the tenon and mortise means may be interlocked between the implement and carrier means, but supported on relatively resiliently laterally displaceable portions of the bodies of the implement and carrier means.

To enable the user to locate and steer the device along a row of teeth when the jaws are out of sight to him, many presently preferred embodiments of the device employ carrier means which have stylus-like means thereon that operatively project into the gap between the jaws to be traceable along the gum line of a row of teeth when the jaws are straddled about the row, transverse thereof, and translated along the row opposite the inside and outside faces of the teeth. In some embodiments, the stylus-like means operatively project into the gap, breadthwise thereof, from points adjacent the jaws of the carrier means. In certain of these, the stylus-like means are supported on the jaws of the carrier means; whereas in other embodiments, the implement and carrier means have oppositely disposed jaws on the bodies thereof, and the stylus-like means are supported on the jaws of the implement. In still other embodiments, the jaws of the implement are operatively spaced apart from one another, crosswise the longitudinal axis of the positioning means, to form a slot therebetween, and the stylus-like means are supported on the jaws of the carrier means and impaled in the jaws of the implement to operatively project into the slot therebetween, breadthwise thereof.

In one group of embodiments, the stylus-like means take the form of pick-like elements which project into the gap, breadthwise thereof, from points adjacent the jaws of the carrier means, and are semi-rigid in character to dislodge debris collected on the gum line of the row of teeth. In another group of embodiments, the stylus-like means take the form of a pair of tenon-like elements which are impaled in the implement to detachably retain the same on the carrier means, and project into the gap, breadthwise thereof, from points on the implement adjacent the jaws of the carrier means. In still another group, the stylus-like means take the form of a pair of semi-rigid pick-like elements which are supported on the jaws of the carrier means and impaled, tenon-like, in the implement to project into the gap, breadthwise thereof, from points on the implement adjacent the jaws of the carrier means, so that they can also dislodge debris collected on the gum line of the row of teeth.

In still further embodiments, the carrier means have brush-like means thereon which are disposed in the gap between the jaws to be applied to the inside and outside faces of the row of teeth when the stylus-like means are traced along the gum line thereof, and the stylus-like means project into the gap, breadthwise thereof, from points on the brush-like means adjacent the jaws of the carrier means. In some embodiments, the brush-like means have fields of bristle that are oppositely disposed to the jaws of the carrier means, and the stylus-like means project within the fields of bristle from points adjacent the jaws of the carrier means. In one group of these embodiments, the implement and carrier means are detachably connected with one another and have oppositely disposed jaws on the bodies thereof. The jaws of the implement are operatively spaced apart from one another, crosswise the longitudinal axis of the positioning means, to form a slot therebetween, and have fields of bristle thereon which project into the slot breadthwise thereof. The stylus-like means take the form of a pair of stylii which project into the slot from points on the jaws of the implement within the fields of bristle thereon. In some of these embodiments, the stylii are supported on the jaws of the carrier means and impaled in the jaws of the implement to project within the fields of bristle thereon. In other embodiments, the stylii are supported on the jaws of the implement itself, to project within the fields of bristle thereon.

It follows from all of this, moreover, that certain presently preferred processes for cleaning teeth with a pair of tooth cleaning jaws which are spaced apart from one another to form a gap therebetween, include the steps of straddling the pair of jaws about a row of teeth, transverse thereof, projecting stylus-like means into the gap between the jaws, and tracing the stylus-like means along the gum line of the row of teeth to locate the jaws, while translating the jaws in unison with the stylus-like means to effect the cleaning operation. Many of these processes employ stylus-like means which are semi-rigid in character to dislodge debris collected on the gum line of the row of teeth. Furthermore, certain processes employ the step of brushing the inside and outside faces of the teeth as part of the tooth cleaning operation; and, in many instances, the faces are brushed by fields of bristle on the jaws which have the stylus-like means projecting therewithin.

As a replaceable or interchangeable item, the tooth cleaning implement often takes the form of a taco shell-like cartridge unit which is inserted in the gap between the jaws and comprises a U-shaped cowling having tooth brushing bristle upstanding on the inner periphery thereof, there being connector means in the device whereby the cartridge unit is detachably connected to the carrier means. The skirts of the cowling are ordinarily disposed opposite the jaws of the carrier means and have fields of bristle upstanding on the relatively inside faces thereof. In addition, one or both of the bight and the corners of the cowling may also have fields of bristle upstanding on the relatively inside faces thereof, and there may also be a field of bristle upstanding on the bight of the cowling at the outer periphery thereof.

Preferably, the bristle in the various fields are discrete individual bristle which are spaced apart from one another in the respective fields of the same.

In many of the presently preferred embodiments of the device the cowling also has tenon-like means thereon, at the outer periphery thereof, and the connector means include mortise-like means on the carrier means which form a male/female joint with the tenon-like means of the cowling. Or, in the alternative, the cowling has mortise-like means thereon, at the outer periphery thereof, and the connector means include tenon-like means on the carrier means which form a male/female joint with the mortise-like means of the cowling.

In one special group of embodiments, the skirts of the cowling also have stylus-like means upstanding on the relatively inside faces thereof, within the fields of bristle thereon. In many of these embodiments, the stylus-like means are semi-rigid to perform as picks.

In still another group of embodiments, the cowling is constructed of reentrantly folded flexible and/or bendable material, and the bristle are monolithic therewith.

In fact, in certain of the presently preferred embodiments of the invention, the device employs a monolithic cartridge-forming module which comprises a substrate of sheet material having three sections that are successively interconnected with one another in a bat-like, spread wing configuration having a memory to sustain the same, but which is sufficiently flexible and/or pliable to enable the substrate to be reentrantly folded about the mid section thereof into a generally U-shaped configuration, there being tooth brushing bristle on one side of the substrate to upstand on the inner periphery of the module at the skirts thereof when the substrate is folded into a generally U-shaped configuration. In certain embodiments, the endmost sections and mid section of the substrate are substantially coplanar. In other embodiments, the endmost sections of the substrate are obliquely angled to the mid section thereof, in the direction of the one side of the substrate.

In many embodiments, there are sets of bristle on the endmost sections of the substrate, at the one side thereof, and the bristle in the respective sets are of varying length so that they have oppositely inclined profiles at the tips thereof, relative to the dimensional plane of the substrate at the mid section thereof. In certain of this latter group of embodiments, there are stylus-like means upstanding on the one side of the substrate within the sets of bristle on the endmost sections thereof. Moreover, in some of them, the stylus-like means are semi-rigid to perform as picks.

Often, the substrate has means on the other side thereof for forming a tenon and mortise joint with a carrier for the module. Also, the other side of the substrate often has tooth brushing bristle upstanding on the mid section thereof.

Many embodiments of the invention employ what, in essence, is a tooth brushing head having a relatively rigid base with a field of elongated, relatively flexible tooth brushing bristle thereon, which are discrete individual bristle and upstand from the base in spaced relationship to one another, with bodies that taper relatively inward of the longitudinal axes thereof, substantially from the base to the tips thereof. In some embodiments, the bodies of the individual bristle have circular cross-sections transverse the longitudinal axes thereof. In other embodiments, the bodies of the individual bristle have polygonal cross-sections transverse the longitudinal axes thereof. In certain embodiments, the bodies of the bristle have diamond shaped cross-sections transverse the longitudinal axes thereof, and are arrayed in diagonal lines in which planar faces of the respective bristle are directly opposed to one another.

In one group of embodiments, the bodies of the individual bristle have a conical shank, the angle of which is increased at the upper tip portion thereof. In another group, the bodies of the individual bristle have a relatively harder shank portion, and a relatively softer tip portion at the top thereof. In still another group, the bodies of the individual bristle are divided into relatively harder and softer sections, longitudinally thereof. In still another, the bodies of the individual bristle have a relatively harder core, and a relatively softer sheath surrounding the same.

In many instances, the bodies of the individual bristle have grooves extending longitudinally thereof.

Additional embodiments have a field of bristle wherein the bodies of the individual bristle vary in hardness from one area of the field to another. Others have a field of bristle which is divided into two spaced portions, and the bodies of the individual bristle vary in hardness from one portion to another.

Typically, the positioning means include an elongaged boom-like extension on the handle having the carrier means at the distal end thereof. In many cases, the boom-like extension is relatively inflexible, crosswise the longitudinal axis of the positioning means, and/or lengthwise the longitudinal axis of the positioning means.

BRIEF DESCRIPTION OF THE DRAWINGS

These features will be better understood by reference to the accompanying drawings which illustrate several of the presently preferred embodiments of the invention as it is applied to cleaning rows of teeth in the mouth of a human being, using a handle which is gripped directly outside of the mouth.

In the drawings:

FIG. 1 is a part perspective view of one embodiment wherein the device is adapted for flossing between pairs of teeth;

FIG. 2 is a part cross-sectional view along the vertical axial plane of the positioning means in the device of FIG. 1;

FIG. 3 is a cross-sectional view along the line 3—3 of FIG. 2;

FIG. 4 is a part cross-sectional view along the line 4—4 of FIG. 2;

FIG. 5 is a part perspective view of another embodiment wherein the device is adapted for brushing rows of teeth with some of the criss-cross action or dynamics discussed earlier;

FIG. 6 is a part side elevational view of the tooth brushing device seen in FIG. 5;

FIG. 7 is a front elevational view of the tooth brushing device seen in FIG. 5;

FIG. 8 is a part plan view of the device when it is in the dead center position thereof;

FIG. 9 is a part cross-sectional view along the line 9—9 of FIG. 8;

FIG. 10 is another part plan view of the device when it is in one phase of its oscillation;

FIG. 11 is a part cross-sectional view along the line 11—11 of FIG. 10 in that phase;

FIG. 12 is a front elevational view of the device when it is in this phase on a tooth;

FIG. 13 is a part plan view of the device when it is in the opposite phase of its oscillation;

FIG. 14 is a part cross-sectional view along the line 14—14 of FIG. 13 in the latter phase;

FIG. 15 is a front elevational view of the device when it is in the latter phase on a tooth;

FIG. 16 is a part perspective view of a third embodiment wherein the device is again adapted to brush with the foregoing dynamics;

FIG. 17 is a part side elevational view of the tooth brushing device seen in FIG. 16;

FIG. 18 is a part cross-sectional, part front elevational view of the device seen in FIGS. 16 and 17;

FIG. 19 is a part cross-sectional, part front elevational view of the carrier means in the last mentioned device;

FIG. 20 is an elevational view of the pick-like tenon and stylus means used in the last mentioned device;

FIG. 21 is a plan view of the latter means;

FIG. 22 is a part perspective view of still another embodiment wherein, however, the tooth brushing device provides both the dynamics and the adjustable grip explained earlier;

FIG. 23 is a part plan view of the device seen in FIG. 22;

FIG. 24 is a front elevational view of the device seen in FIGS. 22 and 23;

FIG. 25 is a part perspective view of a fourth tooth brushing device which also provides the dynamics and adjustable grip explained earlier;

FIG. 26 is a part side elevational view of the device seen in FIG. 25;

FIG. 27 is a part plan view of the device seen in FIGS. 25 and 26;

FIG. 28 is a part front elevational view of the device seen in FIGS. 25-27;

FIG. 29 is an end elevational view of a monolithic cartridge forming module for device of FIGS. 25-28;

FIG. 30 is a bottom view of the module;

FIG. 31 is a part perspective view of the device seen in FIGS. 25-28 when the device is straddled about a row of teeth in the user's mouth, transverse thereof, and translated along the row opposite the inside and outside faces of the teeth;

FIG. 32 is a part front elevational view of the device seen in FIGS. 25-28 when it is applied to a row of teeth in the manner of FIG. 31, with the module of FIG. 29;

FIG. 33 is an end elevational view of another monolithic cartridge forming module for use in the device of FIGS. 25-28;

FIG. 34 is a front elevational view of the module seen in FIG. 33 when it is mounted in the device of FIGS. 25-28;

FIG. 35 is a part plan view of one of the fields of bristle employed in the foregoing modules;

FIG. 36 is a part plan view of an another field of bristle;

FIG. 37 is a part plan view of still another field of bristle;

FIG. 38 is a part plan view of a fourth field;

FIG. 39 is a part plan view of a fifth;

FIG. 40 is a part perspective view of an individual bristle in the field of FIG. 35;

FIG. 41 is a cross-sectional view along the line 41—41 of FIG. 40;

FIG. 42 is a part perspective view of an alternative bristle;

FIG. 43 is a part perspective view of still another bristle;

FIG. 44 is a cross-sectional view along the line 44—44 of FIG. 43;

FIG. 45 is a part cross-sectional perspective view of a fourth bristle; and

FIG. 46 is a cross-sectional view along the line 46—46 of FIG. 45.

BEST MODE FOR CARRYING OUT THE INVENTION

To understand, preliminarily, the general nature of each device and how it is used, reference should be made initially to FIG. 31 wherein the tooth cleaning device 2 illustrated in FIGS. 25-30 is seen in use. Broadly speaking, the device 2 comprises carrier means 4 which are adapted to hold a tooth cleaning implement 6 and to be inserted with the implement in the mouth 8 of a user, and positioned in his mouth adjacent a row of his teeth 10, for application of the implement 6 thereto. It also comprises elongated positioning means 12, including a handle 14, for supporting the carrier means 4 adjacent the user's row of teeth 10. The carrier means 4 are connected with the positioning means 12 adjacent the distal end thereof, and comprise a pair of jaws 16 which are operatively spaced apart from one another crosswise the longitudinal axis of the positioning means, to form a gap 18 therebetween. The pair of jaws 16, in turn, have connector means 20 thereon, whereby the tooth cleaning implement 6 can be detachably connected with the carrier means 4, relatively crosswise of the gap 18 between the jaws. Further reference will be made to the particulars of the device 2 when FIGS. 25–31 are described more fully hereinafter.

Referring first, however, to FIGS. 1–4, it will be seen that, once again, the device 22 illustrated in these Figures comprises carrier means 24 which are adapted to hold a tooth cleaning implement 26, and to be inserted in the user's mouth (not shown) with the same, and positioned adjacent a row of his teeth (not shown) for application of the implement 26 thereto. It also comprises elongated positioning means 28, including a handle 30, for supporting the carrier means 24 adjacent the user's row of teeth. Once again, moreover, the carrier means 24 are connected with the positioning means 28 adjacent the distal end thereof, and comprise a pair of jaws 32 which are operatively spaced apart from one another crosswise the longitudinal axis of the positioning means 28, to form a gap 34 therebetween. The pair of jaws 32, in turn, have connector means 36 thereon, whereby the tooth cleaning implement 26 can be detachably connected with the carrier means 24, relatively crosswise the gap 34 between the jaws.

More particularly, the implement 26 in FIGS. 1–4 takes the form of an elongated string 38 of dental floss, and the connector means 36 are adapted so that the string 38 can be detachably connected to the jaws 32, in a taut condition crosswise of the gap 34. The carrier means 24, in fact, comprise a generally U-shaped, round-nosed carrier head 40 which serves as a truss-like holder for the length of dental floss. In the inverted position shown, the holder 6 has a somewhat flattened, but generally elongated cylindrical arch or bight 42 at the top thereof, with dog-ear-like skirts 44 depending from the opposing sides of the same, at the forward end portion thereof, and an open-ended slot 46 in the gap 34 between the skirts. The positioning means 28, meanwhile, comprise an elongated cylindrical rod 48 which is bayonetted into a deep cylindrical socket 50 in the rear end of the bight 42, and keyed to the same by means of a depending lug 52 and an axially extending groove 54 in the socket 50 and the distal end portion 48' of the rod 48, respectively. Moreover, the connector means 36 not only include a pair of notches 56 in the bottoms of the skirts 44, but also a pair of short, button-like posts 58 upstanding on the top of the head 40, in the vertical axial plane of the socket 50.

To prepare the device 22 for use, a length of the dental floss 38 is wound about the shank 58' of one post 58, and then roved downward about one skirt 44 of the head, through the notch 56 at the bottom thereof, and across the gap 34 between the skirts; whereupon it is roved upward through the notch 56 in the opposing skirt 44, and thence about that skirt to the additional post 58, where the dental floss is brought into a taut condition by winding it about the shank 58' of the latter post 58. When the device 22 is to be put to use in the user's mouth 8, it is applied to a row of teeth 10 in much the same manner as that seen in FIG. 31. That is, the rod 48 is gripped in one hand, and after it has been manipulated to insert the head 40 in the user's mouth, the head is straddled over the row of teeth 10, as in FIG. 31, and then the string 38 is employed to floss between successive pairs of teeth in the much same manner as one would do so by hand alone. Meanwhile, because of its length, the rod 48 serves not only as a handle 30 for the device, but also as a boom-like extension 60 for the same, by which the head 40 can be placed outboard of the handle, in operative position over a row of teeth, while the user's hand remains outside of his mouth. As indicated earlier, however, the handle 30 may be more directly connected with the head 40, and vice-versa, so that this boom effect is eliminated.

In certain alternative versions of the device 22, a closed loop (not shown) of the floss 38 is employed and simply circumposed about the head 40 and snap engaged in the notches 56.

Preferably, the device 22 is also equipped with means for flushing debris from the row of teeth 10 as the floss 38 is employed between pairs of the same, and this further feature can be seen at 62 in FIGS. 1–4. More specifically, the rod 48 is tubular, and there is, therefore, a liquid flow passage 64 in the same on the axis of the rod. The passage 64 has a lateral opening 66 in the same, at a point in the distal end portion thereof, and there is a corresponding opening 68 in the head 40 which registers with the opening 66 of the rod to discharge the passage 64 into the gap 34 between the skirts 44 of the head. The discharge serves to flush debris from the teeth of the user, and is normally supplied by a flexible tube 70 inserted in the proximal end portion of the passage 64. The opposing end of the tube 70 is supplied, in turn, by a water faucet or the like, such as that seen at 72 in FIG. 5, where an adaptor 74 has been applied to the faucet to supply the tube 70 in any one of several ways known in the art.

The device 76 illustrated in FIGS. 5–15 also comprises carrier means 78, and positioning means 80 for the same, which are of the same nature as those described for FIGS. 1–4. Once again, moreover, the head 82 of the carrier means 78 has a generally U-shaped configuration. However, in this instance, the head 82 serves as a clip-like holder for a correspondingly shaped tooth brushing implement 84 which is detachably connected with the head, relatively crosswise the gap 86 between the skirts 88 thereof, by means of a male/female connection 90 at the bight 92 of the head. In this instance, moreover, the head 82 is rotatably mounted on the positioning means 80, as well as axially shiftable in relation to the same, at a neck 94 formed therebetween. The degree of rotation and axial movement between the two, is limited, however, by a pin and slot connection 96 which is arranged in the neck 94, obliquely thereof, to produce oscillatory motion on the part of the head 82, relative to the positioning means 80, when the head is placed on a tooth 10 and the positioning means are reciprocated along the longitudinal axis thereof, at the handle 98 of the same.

More specifically, the head 82 row has a flat planar bight 92 at the top thereof, and broad flap-like skirts 88 depending from the opposing sides of the bight, at a slight flare thereto. At its center, moreover, the bight has a rectangular opening 100 therein, and there is a cylindrical nipple 102 extending rearwardly from the bight, somewhat along the center line of the same. The nipple 102 is deeper in dimension than the bight itself, but commences only at the rear end edge of the bight, so that there is a corbel-like step 104 at the underside of the edge. Meanwhile, the positioning means 80 has a sleeve-like extension 106 on the forward end of the handle 98, and the extension 106 is adapted to telescopically engage about the nipple 102 of the head 82. The handle 98 itself is slightly larger in dimension, but flattened and scalloped along the longitudinal edges thereof, to be readily engageable by the hand of a user. There is also an axially extending bore 108 through the handle, which is counterbored at the forward end 110 thereof, to accommodate the rear end of the nipple 102. The pin and slot connection 96 is formed by a slot 112 in the extension 106 and an upstanding lug 114 on the nipple 102. The lug 114 and slot 112 are slideably interengaged with one another, and, as indicated earlier, the slot is arranged obliquely to the axis of the handle 98, to provide opposing cam surfaces which cause the head 82 to oscillate about the axis of the handle 98 when the head is placed on a tooth and the handle is reciprocated longitudinally of the axis.

The action of the head 82 on a tooth can be seen in FIGS. 8–15. FIGS. 8 and 9 illustrate the dead center position of the head when the lug 114 is midway in the slot 112 of the neck 94. FIGS. 10–12 illustrate the clockwise rotation undergone by the head 82 when the handle 98 is advanced forwardly cf the device; and FIGS. 13–15 illustrate the counterclockwise rotation undergone by the head when the handle is retracted rearwardly thereof.

The oscillatory motion of the head produces a similar motion on the part of the implement 84, and this, in turn, produces a rotary scrubbing effect on each tooth 10 as the device is moved lengthwise of the row of the same. This effect will be explained more fully hereinafter when the character of the implement 84 is addressed more fully.

Once again, the device 76 is preferably equipped to flush debris from the row of teeth as they are scrubbed by the implement 84. More specifically, there is a liquid supply tube 116 inserted in the bore 108 of the handle 98, and the nipple 102 of the head 82 is tubular in cross-section to provide an axial extension 118 for the bore 120 of the tube at the center of the neck 94. The extension 118 is canted, moreover, at the forward end 112 thereof, to open into the bottom of the step 104 under the rear end edge of the head. When the flexible tube 70 from the adaptor 74 is inserted in the rear end of the supply tube 116, the water from the faucet 72 discharges into the gap 86 between the skirts 88 of the head, and operates as a flush medium for debris in the gap, as in the case of the device 22 shown in FIGS. 1–4.

Referring now to the implement 84 itself, it will be seen that it comprises an insertable, reentrantly folded, Taco-shell-like cartridge 124 having a plurality of sea-urchin-like fields 126 of individual bristle 128 upstanding on the cowling 130 thereof, at the inside surfaces thereof. Two of the fields 126' are mutually opposed to one another on the skirts 132 of the cowling, and a third field 126" is disposed on the bight 134 of the same. Smaller fourth and fifth fields 126''' are disposed on the corners 136 of the cowling, and together, the five fields 126 of bristle 128 form a narrow open-ended slot 138 therebetween, for straddling one or more teeth 10 to be cleaned.

Like the head 82 which carries it, the cartridge 124 has a semi-rigid cross-section and is largely form-sustaining, independent of the head. However, as shall be explained, it can be fabricated otherwise, and given form only when it is inserted and secured to the head.

When it is inserted, the cartridge is sized to be telescopically received in the slot 86 of the head, and once inserted, conforms to the slot, but is slightly deeper at the skirts 132 of the same, so as to depend below the mouth of the slot. In addition, the cartridge 124 has a shallow cupola-like tenon 140 upstanding on the top thereof, and an additional field 142 of bristle 128 upstanding on the tenon 140 itself. The tenon 140 and bristle 142 are disposed to telescopically engage in the opening 100 of the head; and the wall of the tenon has a circumferential swale thereabout, and pairs of spaced dogs 144 on the longitudinally extending sides thereof, which are cantilevered over the sides, but resiliently yieldable inward of the same, so that when the cartridge 124 is inserted in the slot 86, the tenon 140 snap engages in the opening 100 of the head and thereby detachably connects the cartridge to the head, and vice-versa.

Referring again to FIGS. 12 and 15, it will be seen that the cartridge 124 is also sized so that the skirts 132 of the same depend to a point adjacent, if not below the gum line 146 of each tooth 10. The opposing fields 126' of bristle on the skirts likewise oppose the gum line of the tooth, and when the cartridge is straddled over a tooth, as shown, not only are the inside and outside faces 148 of the tooth swept by the bristle, but also the gum 150 therebelow as well. Meanwhile, the bristle 126" at the top 134 of the cartridge sweep the top of the tooth, and the bristle 126''' in the corners 136 sweep the cusps 152 of the tooth. The action is both parallel to the gum 150 and crosswise thereof, due to the action of the pin and slot connection 96 in oscillating the head 82 when the user reciprocates the handle 98 of the device lengthwise of the gum. The outside bristle 142 can serve, meanwhile, as a tongue wipe; or if desired, as a conventional toothbrush, when one is needed to clean the teeth in a more conventional manner.

The cartridge 124 is replaceable in that, when desired, the tenon 140 can be displaced from the opening 100 of the head, to "pop" the cartridge out of the head. Or in the alternative, the user can pinch the depending tips 132' of the skirts 132 between his thumb and forefinger, while wedging one or both nails of the same between the skirts 132 of the cartridge and the skirts 88 of the head, to grasp and pull the cartridge from the head.

The cartridge carrying device 154 seen in FIGS. 16–21 is similar to that seen in FIGS. 5–15, and once again comprises interconnected carrier means 156 and positioning means 158 for the cartridge 160 of the same. The connection 162 between the carrier means and positioning means is once again a male/female connection, moreover, but employs a nipple 164 on the forward end of the handle 166 of the positioning means 158, and a sleeve 168 on the rear end of the head 169 of the carrier means 156. The pin and slot connection 170 in the neck 172 is detachable in this instance, moreover, in that the pin 174 is seated in a small socket 176 and captured by a lip 178 on the rim thereof. The lip 178 overlies a flange 180 on the lower end of the pin, and there is a coiled spring 182 caged within the socket, below the pin 174, to bias it into engagement with the lip 178. When it is desired to separate the head 169 from the positioning means 158, or vice-versa, the pin 174 can be depressed against the bias of the spring 182, to enable the nipple 164 to be removed from the sleeve 168, and vice-versa.

The cartridge 160 is also similar to that seen in FIGS. 5–15, but it has fewer fields 184 of bristle 128, and is retained in the slot 186 of the head 169 by additional tenon and mortise fastening means 188 thereon. As seen, the skirts 190 of the head are now divided into three flaps 192 apiece, and the intermediate flap 192' of each skirt has an opening 194 therein adjacent the bottom of the same. The indentations 196 dividing the flaps, are angled relatively toward one another, moreover, so that each intermediate flap 192' is capable of being flexed slightly out of the plane of the respective skirt 190. The skirts 198 of the cartridge 160, meanwhile, are slightly longer than those of the head 169, so that there are, once again, depending tips 198' of the same with which the user can pinch the skirts 198 together when removing the cartridge 160 from the head.

As seen in FIGS. 17 and 18, there are apertures 200 in the skirts 198 of the cartridge 160 which register with those, 194, in the skirts 190 of the head, when the cartridge is engaged in the slot 186 of the head. The additional fastening means 188 make use of these holes 200, 194, and take the form of pick-like fastening studs 202 which have flat heads 204, and elongated bodies 206 that taper to a point at the forward ends 207 thereof. The bodies 206 of the studs 202 also have bulbous waists 208, and relatively recessed necks 210 between the waists 208 and heads 204 thereof. The pointed ends 207 of the studs are serrated or fluted, moreover, to assist in a further function given the studs in the device, as shall be explained hereinafter.

When the cartridge 160 has been engaged in the slot 186 of the head 169, and the apertures 200 are in registry with the openings 194 in the head, the studs 202 are inserted in the openings 194, point 207 first, and then bayonetted through the apertures 200 into the fields 184 of bristle thereinside. The apertures 200 are adapted to slideably receive the bulbous waists 208 of the studs, but the openings 194 in the head are slightly smaller in diameter, and when the waists of the studs clear the openings, the studs snap engage in the same, to "rivet" the cartridge to the head while it is, at the same time, snap engaged in the opening 100 at the top of the head.

When the user desires to remove the cartridge 160 from the head, for example, to replace it with another cartridge, once again he can insert his fingernails or a knife-like instrument between the skirts 198, 190 of the cartridge and the head, to free the skirts 198 of the cartridge from the waists 208 of the studs, while at the same time, pinching the skirts 198 together to enable the cartridge to be withdrawn from the head over the inclined tips 207 of the studs. The intermediate flaps 192' of the skirts 190 of the head flare outwardly, meanwhile, to incline the studs more downwardly to the mouth of the head and facilitate the task of removing the cartridge.

The device does not, in fact, require a separate head and cartridge for the same, and as shall be explained, there is an advantage in using a single-piece head and cartridge in lieu of the two-piece head and cartridge illustrated in FIGS. 1-21. Referring now to FIGS. 22-24, it will be seen that the carrier means 212 in this instance comprise a pair of jaws 214 which are formed on the forward end portions of a pair of tong-like arms 216 that are cantilevered, boom-like, from sockets 217 in the forward end 218' of the handle 218 of the positioning means 220. The arms 216 are elongated, resiliently flexible, and cantilevered from the handle 218 at equal angles to the axis of the positioning means 220, so as to be acutely angularly interconnected with one another. The arms 216 also have corresponding L-shaped configurations, the laterals 222 of which depend from the forward ends 214 of the arms and provide means whereby a cartridge-type tooth cleaning implement 224 can be detachably connected with the arms. The handle 218, meanwhile, is again elongated, cylindrical and tubular in cross-section, to provide a liquid flow passage 226 therein for flushwater flow through the device, if desired, although no specific debris flushing means are shown for the device. The handle 218 is also chamfered at its ends 218', 218" and a feed tube 228 is secured to the proximal end portion 218" of the handle to supply flush water for the same, should provision be made for flushing away debris.

The implement 224, when in operative disposition, has a generally U-shaped configuration, like the cartridge 26, 84, 160 and heads 32, 82, 169 of FIGS. 1-21. But, in this instance, the implement 24 provides its own head, and vice-versa, and is mounted crosswise the gap 230 between the pair of jaws 214, using a pair of laterally projecting cleats 232 on the skirts 234 of the implement. Once again, the implement 224 comprises a reentrantly folded, Taco-shell-like cartridge 236 similar to that seen in FIGS. 5-21, but in this instance, the cowling 238 of the cartridge is more flexible and/or bendable so that the gap 240 between the skirts 234 of the same can be opened and closed by flexing the skirts relatively toward and away from one another. Referring again to FIGS. 22-24, it will be seen that the cleats 232 on the skirts 234 of the cowling, have vertically oriented sockets 242 therein which are adapted to receive the laterals 222 of the arms 216 as shown. The laterals 222 forcibly engage in the sockets, and when they are engaged, the cartridge is fully supported between the arms. However, as an additional means of support, there is also a raised cupola-like berm 244 on the bight 246 of the cowling, and the berm 244 has a threaded hole 248 in the rear end thereof, for a threaded support rod 250 extending from the handle 218. The hole 248 is opposed by a similarly threaded hole 252 on the forward end 218' of the handle, between the sockets 217 for the arms 216, and the rod 250 is interposed between the holes 252, 248 to support the cartridge 236 at the ends of the arms, as shown.

The rod 250 also serves as a guide for a slide bar 254 which has alternately disposed grooves 256 and 258 in the upper and lower edges thereof, to interfit over and between the arms 216 about the rod 250 as shown. The bar 254 is slideably engaged about the rod in the top-opening groove 256 thereof, and slideably engaged about the arms in the bottom opening grooves 258 thereof. In use, the bar 254 is reciprocated lengthwise of the arm assembly, either to cam the arms 216 relatively toward one another, or to release them so that they may resume their original disposition under the bias inherent in the resiliency of the arms. The cowling 238, in turn, is flexed to open and close the gap 240 between the skirts 234 of the cartridge, crosswise the slot 260 therebetween. And, when the device 220 is straddled over a row of teeth 10 in the manner of FIG. 31, the adjustment operates to vary the "grip" of the device, to allow, in turn, for variation in tooth width from one user to another, and/or for the wear which the bristle 262 of the cartridge will undergo over the life of the device.

The device 2 illustrated in FIGS. 25-31 is similar to that seen at 264 in FIGS. 22-24. However, in lieu of a forked, boom-like carrier means 212, the device 2 in FIGS. 25-30 has a single axially extending arm 266 cantilevered from the handle 14 thereof, and the distal end portion 268 of the arm 266 is bifurcated to form juxtaposed halves 270 and 272 which are resiliently flexible and separated from one another by a slot 274 which is contoured to provide several functions for the device. At the mouth of the slot 274, the distal end portion 274' of it has a rectangular configuration to accommodate the additional field 276 of bristle 128 on a brush-topped cartridge, such as was provided in FIGS. 5-21. At the bottom of the slot, the proximal end portion 274" of it has a part-annular or sectoral configuration, and between the two end portions, there is a pair of opposing benches 278 which divide the slot 274 midway thereof.

In addition to being bifurcated, the arm 266 also has a pair of legs 280 projecting laterally therefrom, obliquely downwardly of the arm, at the distal end portion 268 thereof. And installed in the slot 274, between the halves 270, 272 of the arm, is a notched or I-sectioned slide bar 282 which is interengaged with the arm to slide lengthwise of the same, in the proximal end portion 274" of the slot. When the bar 282 is reciprocated rearwardly of the arm, the waist section 284 of the same operates to separate the halves 270, 272; whereas, when the bar 282 is reciprocated forwardly of the arm, the halves tend to relax and reapproach one another, due to the resilient nature of the flexibility in them. The cam action is opposed to that in FIGS. 22-24, therefore, in that a male slide 282 is employed, to cause the halves to deflect relatively away from one another; whereas in FIGS. 22-24, the female slide bar 254 worked against the "memory" of arms 216 tending to resume their deflection, relatively apart from one another, when relaxed.

The cartridge 6 employed in the embodiment of FIGS. 25-31 is similar to that employed in FIGS. 22-24. And, like the cartridge 236 in FIGS. 22-24, it may be preformed to a generally U-shaped configuration having the required flexure at the skirts 286 thereof; or it may be fabricated as a flexible and/or pliable module which is flexed and/or bent into this configuration only at the time of use. Furthermore, if it is of the latter type, it may be fabricated to assume the preliminary bat-like, spread wing configuration shown in FIGS. 29 and 30, or the preliminary bat-like, spread wing configuration shown in FIG. 33. In either case, when the cartridge is put to use, it is flexed and/or bent out of memory into the reentrantly folded condition of FIG. 28, in the case of that type shown in FIGS. 29 and 30, or into the reentrantly folded condition of FIG. 34, in the case of that type shown in FIG. 33. In both cases, however, the cartridge 236 or 6 splays into the operative tooth engaging condition shown in FIG. 32, when the cartridge is inserted in a mouth 8 and straddled over a row of teeth 10 in the manner of FIG. 31, as shall be explained.

More particularly, the cartridge 6 shown in FIGS. 25-31 comprises a substrate 288 of flexible and/or pliable sheet material, such as is seen in FIGS. 29 and 30, and having the swept-wing appearance or outline shown in FIG. 30 when viewed from the bottom. On the bottom, there are five spaced sets 290 of bristle 128, including a rectangular set 292 extending widthwise of the mid section 288' of the substrate. To each side of it, on the wings 288" of the substrate, there are matching truncated dogleg-shaped sets 294 of bristle, and these, in turn, are accompanied by matching truncated rectangular sets 296 of bristle on the outlying ends of the wings 288". The bristle 292 at the mid section 288' are of equal length, so as to have a flat or planar profile at the top. They are also accompanied by a matching set 298 of bristle 128 on the top side of the substrate, corresponding to that seen at 142 and 184' in the embodiments of FIGS. 5-15 and 16-21. The bristle 294 and 296 on the wings 288" of the substrate, meanwhile, are of varying length, and as seen in FIGS. 29 and 33, have oppositely inclined profiles at the top, relative to the dimensional plane of the substrate at the mid section 288' thereof.

Like the cartridge 236 in FIGS. 22-24, the cartridge 6 in FIGS. 25-31 also has laterally projecting socket-forming cleats 300 on the skirts 286 thereof, although the sockets 302 of the present cleats are more pocket-like to accommodate the broader legs 280 of the arm 266 of the device 2. Otherwise, the cartridge 6 is mounted on the arm in much the same manner as the cartridge 236 was mounted on the arms 216 in FIGS. 22-24. That is, having flexed and/or bent the substrate 288 into a generally U-shaped configuration in the manner of FIGS. 28 or 34, the resulting cartridge is inserted into the slot 274 between the legs 280, as the legs themselves are bayonetted into the pockets 302 of the cleats 300 to detachably connect one to the other. The cartridge 6 is oriented in the slot 274, moreover, to angle the swept edges 304 of the substrate forwardly of the device, as seen in FIGS. 25 and 26.

When the device is gripped by the handle 14 and the cartridge 6 is straddled about a row of teeth 10 and then translated along the length of the row in the manner of FIG. 31, the cartridge performs as a tooth cleaning head which grips the teeth between the skirts 286 thereof and then adjusts its grip in accordance with the variance in the diameter of the teeth from tooth-to-tooth. As seen in FIG. 28, the cartridge 6 has three distinct sections in the body thereof comprising the spaced skirts 286, and the midsection 309 therebetween, which are serially interconnected with one another along an axis 301 extending from one half 270 or 272 of the arm 266 to the other, crosswise the length of the slot 274 therebetween. The cartridge 6 also has additional portions 313 thereof which are interposed between the respective skirts 286 and the midsection 309, axially of the cartridge, and connected with the midsection and the respective skirts at 307 and 317, respectively. In the reentrantly folded condition of the cartridge, the tooth cleaning sides 128 of the skirts are folded relatively toward one another, but spaced apart from one another by a gap 240 (FIG. 28) whose mouth lies opposite the midsection 309 of the cartridge for the introduction of the teeth 10 to the gap. Meanwhile, the skirts 286 are capable of reciprocating in relation to one another crosswise of the slot 274 because the halves 270, 272 of the arm 266 are resiliently flexible in relation to one another crosswise of the slot. Moreover, the legs 280 of the arm 266 are operable to yieldably bias the skirts relatively toward one another crosswise of the slot, and given a setting of the slide bar 282 such as that seen in FIGS. 27 and 31, the skirts are yieldably biased relatively toward one another to the extent that the user must relatively forcibly wedge the teeth between the tooth cleaning sides of the skirts to introduce the teeth to the gap 240 through the mouth thereof when the cartridge is straddled about a row of teeth in the manner of FIG. 31. Compare FIGS. 28 and 34 on one hand, wherein the skirts 286 are seen in the normally relaxed but yieldably biased condition thereof, and FIG. 32 on the other, wherein the user has relatively forcibly wedged the tops of the teeth 10 into the gap 240 between the skirts against the bias on the skirts. Thereafter, when the cartridge 6 is translated along the length of the row, the midsection 309 and additional portions 313 of the cartridge form an articulated linkage between the skirts which can flex in relation to the halves 270, 272 of arm 266 to preserve the bias on the skirts while the cartridge adjusts to the varying diameters of the teeth crosswise of the slot. This follows from the fact that the skirts 286 are interposed between the legs 280 of the arm 266 at the opposing sides of the slot 274, and are connected with the legs at points on the opposite sides of the connections 317 from the connections 307, so that the added portions 313 are cantilevered into the slot 274 from the connections 317 and flexibly interposed in the slot between the skirts and the midsection to enable the midsection and added portions of the cartridge to flex in such a way as to preserve the bias on the skirts while the cartridge adjusts to the varying diameters of the teeth crosswise of the slot. Throughout this time, moreover, the bristle 128 in the fields or sets 294, 296 of the same are angled to the gum 150 of the teeth 10 at approximately 45 degrees, as seen in FIG. 32.

Additionally, when the cartridge 6 is pressed down on the teeth to the extent that the closely captured and directly opposing field of bristle 311 on the inside of the midsection 309 engage the tops of the teeth, and the cartridge is translated along the length of the row in this condition—that is, so to speak, "monorailed" along the row—the field of bristle 311 forms a guide bearing for the cartridge, which movably engages the tops of the teeth to determine the penetration of the teeth in the gap 240 and the extent to which the skirts 286 overlie the faces of the teeth in the direction of the gum 150. Yet, because the field 311 is independent of the skirts and disposed in the space between the teeth and the midsection 309, the presence of the field does not prevent the skirts from flexing in relation to the midsection as indicated. Moreover, because the field is resiliently yieldable in nature, a degree of sponginess or "play" is permitted between the midsection and the tops of the teeth, which not only allows the user to adjust the penetration and overlie, but also to monorail the cartridge along the row of teeth with greater ease and comfort.

The studs 202 used in the device of FIGS. 16–21 are not randomly disposed, sized or shaped to serve solely as rivets. To the contrary, they are selectively positioned, sized and shaped to extend within the fields 184 of bristle 128 on the skirts 198 of the cartridge 160 at points where they can also serve as stylii for tracing the gumlines 146 of the teeth to be scrubbed, as seen in FIG. 32. That is, the tips 207 of the studs 202 are sufficiently hard and semirigid to operate as a pointed tool with which the user can sense the location and angle of the bristle when a cartridge 160 is straddled over a row of teeth and translated along the length of the same in the manner of FIG. 31. And, in sensing the continued presence of the tips 207 of the studs as they trace along the lines of his gum, he can also be assured that the cartridge remains properly engaged over the row of teeth, and that the bristle 184 are properly angled, not only to the teeth 10, but also to the gums 150 therebelow. This, in turn, assures him that the scrubbing action will be complete and thorough with respect to both his teeth and his gums. It also assures him that any "moat-like" pockets (not shown) between the gum and the teeth, will be raked by the tips of the studs, to remove debris from the same while the teeth and gum are being scrubbed by the bristle. In this sense, then, the studs 202 operate not only as rivets, but also as stylii and "tooth picks" as well.

The cartridges 6 are preferably molded from a polymeric material, and are molded as a monolith of cowling and bristle alike. Furthermore, stud-like, pick-like stylii 305 are preferably molded into the monolith, together with the cowling and bristle, at points between the fields 294 and 296, as shown.

The cartridge 6' shown in FIGS. 32–34 has the advantage of producing the proper 45° angulation of bristle to teeth and gums, without complicating the molding procedure. Referring to FIGS. 32–34, it will be seen that the cowling 306 of the cartridge 6' is molded into a drop winged configuration in which the skirts 308 are angled to the bight 310 of the cowling when the cartridge exits from the mold. Yet, because the bristle 312 on the wings or skirts 308 are angled obliquely to the wings, rather than perpendicular to the same, as in FIGS. 25–31, the bristle 312 also readily exit from the mold (not shown) in the close of the molding operation.

As indicated earlier, the bristle 128 are discrete individual bristle which upstand from the cowling 288 in spaced relationship to one another; and as seen in FIGS. 35–39, the bristle may be spaced apart from one another in various patterns. The individual bristle may also have various cross-sections, as seen in FIGS. 35–39. These include the tapered conical cross-section 128' seen in FIG. 35, the square but tapered cross-section 128" seen in FIG. 36, the triangular but tapered cross-section 128'" seen in FIG. 37, and the diamond shaped but tapered cross-section 128'" seen in FIG. 38. The tapered conical cross-section 128' of FIG. 35 is capable of the maximum field density, but when the cross-section is varied from a circular one, it can be maximized still further than those shown in FIGS. 36–38, for example, by concentrating the individual bristle 128 in the diagonal pattern of FIG. 39.

The individual bristle 128 may also vary in themselves. Referring to FIGS. 40–46, it will be seen that they may have a conical shank 314, the angle of which is increased at the upper tip portion 314' thereof, and in addition, the exteriors 316 of which are longitudinally serrated or fluted as shown. Or the individual bristle 128 may have a dual composition, such as a relatively harder base or shank portion 318, and a relatively softer tip 320 at the top thereof, as in FIG. 42; or relatively harder and softer longitudinal sections 322 and 324, as seen in FIGS. 43 and 44; or a relatively harder core 326 and a relatively softer sheath or shell 328 surrounding the same, as in FIGS. 45 and 46.

Typically, the relatively softer material has a Shore A scale durometer of 25–50, and the relatively harder, one of 40–80. Many thermoplastic elastomers can be used in producing the required semi-rigid, yet resilient character needed to make the two materials both functional and compatible. For example, certain olefinic and styrenic elastomers have been employed, as have certain polyurethanes. In fact, baby bottle nipple material often has the required flexural strength, flexural modulus, and water absorption—as well as Shore hardness—to make it suitable for the bristle and/or bristle components.

Additional embodiments also employ fields of bristle which vary in hardness from one area of a field to another, or from one field to another. But these features cannot be illustrated in drawings of the type which accompany the present specification.

Often, the cartridge or cartridges shown, are made up in a range of modules having, among them, all of the tooth cleaning functions a user may need to maintain his teeth from day to day, including ones needed to address certain special conditions, such as certain periodontal conditions.

This Application is a continuation in part of my earlier filed copending application Ser. No. 937,554 filed on Dec. 4, 1986 and entitled TOOTH BRUSH AND GUM MASSAGER WITH WATER SPRAY.

I claim:

1. In a straddle-type tooth cleaning device which comprises:

carrier means adapted for insertion in the mouth of the person whose teeth are to be cleaned, an implement that is operatively connected with the carrier means for cleaning the teeth, and elongated positioning means, including a handle, for supporting the carrier means adjacent a row of teeth while the implement is applied thereto, the carrier means comprising a pair of elongated arms which project from the distal end of the positioning means in generally spaced parallel relationship to one another, with an elongated slot extending therebetween, and are rigidly interconnected with the positioning means so as to form relatively rigid extensions of the same, longitudinally thereof, the implement comprising an operatively taco shell shaped cleaning head which is operatively connected with the arms to straddle the slot at the outboard end portions of the arms on an axis of the implement extending from arm to arm crosswise the length of the slot, the cleaning head having three sections in the body thereof comprising a pair of spaced wings, and a midsection in the space therebetween, which are serially interconnected with one another along the aforesaid axis of the implement, the head also having tooth cleaning means on corresponding sides of the wings and being operatively arranged on the arms so that the wings are reentrantly folded about the midsection transverse the axis of the implement, with the tooth cleaning sides thereof folded relatively toward one another, but spaced apart from one another by a gap having a mouth opposite the midsection of the head for the introduction of the teeth to the gap, the cleaning head having additional portions thereof which are interposed between the respective wings and the midsection thereof, axially of the implement, and the respective additional portions being connected with the midsection and the wings at pairs of spaced first and second connections, respectively, the improvement wherein:

the wings of the head are operatively reentrantly folded about the midsection at the first connections, are interposed between the arms at the opposite sides of the slot so that the tooth cleaning sides thereof are opposed to one another crosswise of the slot, and are connected with the outboard end portions of the arms at a pair of third connections which are formed on the bodies of the wings at the opposite sides of the second connections from the first connections in the head, axially of the implement, so that the wings project laterally outwardly from the arms and give the head a taco shell shaped configuration, the wings are capable of reciprocating in relation to one another axially of the implement, means in one of the pairs of first and third connections are operable to yieldably bias the wings relatively toward one another axially of the implement to the extent that when the head is straddled about a row of teeth, the user must relatively forcibly wedge the tops of the teeth between the tooth cleaning sides of the wings to introduce the teeth to the gap through the mouth thereof, and the added portions of the head are cantilevered into the slot from the second connections and flexibly interposed in the slot between the wings and the midsection so that when the head is straddled about a row of teeth and the wings reciprocate in relation to one another axially of the implement as the head is translated along the length of the row of teeth, the midsection and added portions of the head form an articulated linkage between the wings which can flex in relation to the arms to preserve the bias on the wings while the head adjusts to the varying diameters of the teeth axially of the implement.

2. The tooth cleaning device according to claim 1 wherein the outboard end portions of the arms have jaws projecting laterally outwardly therefrom, the wings have recesses in the bodies thereof at points on the opposite sides of the second connections from the first connections in the head, axially of the implement, and the jaws are operatively inserted in the recesses of the wings to form the third connections and yieldably bias the wings relatively toward one another axially of the implement, and wherein the outboard end portions of the arms are resiliently flexible in relation to one another axially of the implement, to enable the wings to reciprocate in relation to one another axially of the implement when the head is straddled about the row of teeth and translated along the length of the row.

3. The tooth cleaning device according to claim 2 wherein the recesses take the form mortises extending within the bodies of the wings on parallels to the tooth cleaning sides thereof, and opening in the directions of the outboard end portions of the arms at the aforesaid points on the opposite sides of the second connections from the first connections in the head.

4. The tooth cleaning device according to claim 3 wherein the mortises are defined by cleats disposed on the outer periphery of the wings when the wings are in the reentrantly folded condition thereof.

5. The tooth cleaning device according to claim 4 wherein the respective jaws are releasably engaged with the mortises in interference fits.

6. The tooth cleaning device according to claim 4 wherein the respective jaws are adapted to be bayonetted into the mortises at the end portions thereof.

7. The tooth cleaning device according to claim 1 wherein the arms project from the distal end of the positioning means on opposing sides of the longitudinal axis thereof, and the device further comprises drive means which are interconnected with the arms at points in the slot between the head and the distal end of the positioning means and reciprocable along parallels to the longitudinal axis of the positioning means to reciprocate the wings in relation to one another when the head is straddled about the row of teeth and translated along the row opposite the inside and outside faces of the teeth.

8. The tooth cleaning device according to claim 7 wherein the arms are reciprocable in relation to one another transverse the longitudinal axis of the positioning means and there are cam means operatively interposed between the drive means and the arms to reciprocate the arms and thus the wings in relation to one another when the drive means are reciprocated along parallels to the longitudinal axis of the positioning means.

9. The tooth cleaning device according to claim 8 wherein the arms are cantilevered from the distal end of the positioning means, axially thereof, and the drive means include a manually driven member which is slideably engaged on the device to be reciprocated along the axis of the positioning means.

10. The tooth cleaning device according to claim 9 wherein the arms are resiliently flexible and have cam surfaces on the relatively remote sides thereof which are disposed at an acute angle to one another, and the drive member takes the form of a drive element which is circumposed about the surfaces and slideably engaged with the same to flex the arms relatively toward one another when the element is reciprocated relatively away from the apex of the angle between the surfaces.

11. The tooth cleaning device according to claim 9 wherein the arms are resiliently flexible and have cam surfaces on the relatively adjacent sides thereof which are disposed at an acute angle to one another, and the drive member takes the form of a drive element which is interposed between the surfaces and slideably engaged with the same to flex the arms relatively away from one another when the element is reciprocated relatively toward the apex of the angle between the surfaces.

12. The tooth cleaning device according to claim 1 wherein the arms project from the distal end of the positioning means on opposing sides of the longitudinal axis thereof, and the device further comprises retainer means which are interconnected with the arms at points in the slot between the head and the distal end of the positioning means and reciprocable along parallels to the longitudinal axis of the positioning means to selected positions in each of which they are operable to yieldably bias the wings into a predetermined separation therebetween having a desired grip on the teeth.

13. The tooth cleaning device according to claim 12 wherein the arms are reciprocable in relation to one another transverse the longitudinal axis of the positioning means and there are cam means operatively interposed between the retainer means and the arms to reciprocate the arms and thus the wings in relation to one another when the retainer means reciprocated along parallels to the longitudinal axis of the positioning means.

14. The tooth cleaning device according to claim 12 wherein the arms are cantilevered from the distal end of the positioning means, axially thereof, and the retainer means include a manually driven member which is slideably engaged on the device to be reciprocated along the axis of the positioning means.

15. The tooth cleaning device according to claim 14 wherein the arms are resiliently flexible and have cam surfaces on the relatively remote sides thereof which are disposed at an acute angle to one another, and the drive member takes the form of a drive element which is circumposed about the surfaces and slideably engaged with the same to flex the arms relatively toward one another when the element is reciprocated relatively away from the apex of the angle between the surfaces.

16. The tooth cleaning device according to claim 14 wherein the arms are resiliently flexible and have cam surfaces on the relatively adjacent sides thereof which are disposed at an acute angle to one another, and the drive member takes the form of a drive element which is interposed between the surfaces and slideably engaged with the same to flex the arms relatively away from one another when the element is reciprocated relatively toward the apex of the angle between the surfaces.

17. The tooth cleaning device according to claim 1 wherein the head takes the form of an operatively taco shell shaped cartridge unit which is operatively inserted in the slot between the arms and interconnected with the arms at the skirts thereof.

18. The tooth cleaning device according to claim 17 wherein the skirts have mortises in the bodies thereof which extend substantially along parallels to the dimensional planes of the skirts and open in the direction of the bight portion of the cartridge unit, and the arms have jaws thereon which project laterally of the arms at the outboard end portions thereof and are operatively engaged with the skirts at the mortises to yieldably bias the skirts relatively toward one another to the extent that the cartridge unit retains its taco shell shaped configuration in use, yet the skirts are capable of flexing in relation to one another crosswise of the slot between the arms to accommodate to variance in the diameter of the teeth.

19. The tooth cleaning device according to claim 18 wherein the cartridge unit comprises a sheet of flexible material which is reentrantly folded about the midsection thereof into a generally U-shaped configuration.

20. The tooth cleaning device according to claim 19 wherein the sheet has a substantially continuously, uninterrupted cross-section, including at the fold lines thereof.

21. The tooth cleaning device according to claim 1 wherein the arms terminate in spaced relationship to one another, 22. The tooth cleaning device according to claim 1 wherein the arms are fixed on the distal end of the positioning means.

23. The tooth cleaning device according to claim 1 wherein the positioning means include an elongated boom-like extension on the handle having the carrier means on the distal end thereof.

24. The tooth cleaning device according to claim 23 wherein the boom-like extension is relatively inflexible crosswise the longitudinal axis of the positioning means.

25. The tooth cleaning device according to claim 1 wherein the wings have a swept-back configuration.

26. The tooth cleaning device according to claim 1 wherein the wings and the arms are detachably interconnected with one another.

27. The tooth cleaning device according to claim 1 wherein the tooth cleaning means comprise brush-like means which are disposed on the wings to be applied to the inside and outside faces of the row of teeth.

28. The tooth cleaning device according to claim 1 wherein the tooth cleaning means take the form of stylus-like means which are disposed on the wings to be traceable along the gum lines of the row of teeth when the head is straddled about the row and translated along the row opposite the inside and outside faces of the teeth.

29. The tooth cleaning device according to claim 28 wherein the stylus-like means take the form of pick-like elements which are semi-rigid in character to dislodge debris collected on the gum lines of the row of teeth.

30. The tooth cleaning device according to claim 28 wherein the tooth cleaning means also comprise brush-like means which are disposed on the wings to be applied to the inside and outside faces of the row of teeth when the stylus-like means are traced along the gum lines thereof.

31. The tooth cleaning device according to claim 30 wherein the brush-like means have fields of bristle that are oppositely disposed to one another, and the stylus-like means project within the fields of bristle.

32. The tooth cleaning device according to claim 1 wherein the head takes the form of a cowling of reentrantly folded flexible material having fields of bristle upstanding on the wings thereof, at the inside of the cowling, and pick-like elements which project within the fields of bristle to dislodge debris collected on the gum lines of the row of teeth, the bristle and pick-like elements being monolithic with the flexible cowling material.

33. The tooth cleaning device according to claim 32 wherein the bristle in the respective fields of the same are of varying length so that they have oppositely inclined profiles at the tips thereof, relative to the dimensional plane of the cowling at the midsection thereof.

34. The tooth cleaning device according to claim 1 wherein the head also has additional tooth cleaning means on the midsection thereof.

35. The tooth cleaning device according to claim 34 wherein the additional tooth cleaning means include tooth cleaning bristle on the outer periphery of the head at the midsection thereof.

36. The tooth cleaning device according to claim 1 further comprising means forming a guide bearing for the head on the inside of the midsection which is independent of the wings and movably engageable with the tops of the teeth to determine the penetration of the teeth in the gap and the extent to which the wings overlie the faces of the teeth in the direction of the gum when the implement is monorailed along the length of the row by the user.

37. The tooth cleaning device according to claim 36 wherein the means forming the guide bearing are resiliently yieldable in nature.

38. The tooth cleaning device according to claim 36 wherein the means forming the guide bearing take the form of a field of bristle upstanding on the inside of the midsection.

* * * * *

UNITED STATES PATENT AND TRADEMARK OFFICE
CERTIFICATE OF CORRECTION

PATENT NO. : 5,137,039
DATED : August 11, 1992
INVENTOR(S) : Ronald W. Klinkhammer It is certified that error appears in the above-identified patent and that said Letters Patent is hereby corrected as shown below:

Column 22, line 2 of Claim 3, after "form" insert --of--.
Column 23, line 7 of Claim 13, after "means" insert --are--.

Signed and Sealed this

Twenty-first Day of September, 1993

Attest:

BRUCE LEHMAN

Attesting Officer     Commissioner of Patents and Trademarks